United States Patent [19]
Jang

[11] Patent Number: 6,113,627
[45] Date of Patent: Sep. 5, 2000

[54] TUBULAR STENT CONSISTS OF HORIZONTAL EXPANSION STRUTS AND CONTRALATERALLY ATTACHED DIAGONAL-CONNECTORS

[76] Inventor: G. David Jang, 30725 Eastburn La., Redlands, Calif. 92374

[21] Appl. No.: 09/241,320

[22] Filed: Feb. 1, 1999

Related U.S. Application Data

[60] Provisional application No. 60/073,523, Feb. 3, 1998.
[51] Int. Cl.$^7$ ...................................................... A61F 2/06
[52] U.S. Cl. .................................................................. 623/1
[58] Field of Search ..................................... 606/108, 191, 606/192, 194, 195, 198; 623/1, 11, 12

[56] References Cited

U.S. PATENT DOCUMENTS

| | | | |
|---|---|---|---|
| 5,836,964 | 10/1999 | Richter et al. | 623/1 |
| 5,964,798 | 10/1999 | Imran | 623/1 |

FOREIGN PATENT DOCUMENTS

| | | | |
|---|---|---|---|
| 297 02 671 | 5/1997 | Germany | A61F 2/04 |
| WO 97/32543 | 9/1997 | WIPO | A61F 2/06 |
| WO 99/01088 | 1/1999 | WIPO | A61F 2/06 |

*Primary Examiner*—Michael Buiz
*Assistant Examiner*—Vy Q. Bui
*Attorney, Agent, or Firm*—Wilson Sonsini Goodrich & Rosati

[57] ABSTRACT

A circumferentially connected stent in a non-expanded state with a longitudinal axis, including a plurality of expansion struts forming a first expansion column, the first expansion column including a first expansion strut, a second expansion strut and a first joining strut. The first joining strut couples a distal end of the first expansion strut to a distal end of the second expansion strut, and the first expansion strut has a stepped distal portion and the second expansion strut has a stepped proximal portion. A plurality of expansion struts defines a second expansion column, and the second expansion column includes a first expansion strut, a second expansion strut and a first joining strut which couples a distal end of the first expansion strut to a distal end of the second expansion strut, and the first expansion strut has a stepped proximal portion and the second expansion strut haves a stepped distal portion. A first serial connecting strut column is formed of a plurality of serial connecting struts and includes a first serial connecting strut. The first serial connecting strut column couples the first expansion column to the second expansion column.

49 Claims, 7 Drawing Sheets

TUBULAR STENT CONSISTS OF HORIZONTAL EXPANSION STRUTS AND CONTRALATERALLY ATTACHED DIAGONAL-CONNECTORS

This application claims benefit to U.S. provisional application Ser. No. 60/073,523 filed Feb. 3, 1998.

BACKGROUND OF THE INVENTION

1. Field of the Invention

This invention relates to intravascular stents, and more particularly to an intravascular stent, which provides easy introduction through tortuous sections of vessels but this invention can be used as an intraluminal scaffolding device in any tubular body anatomy.

2. Description of the Related Art

Angioplasty, either coronary or general vascular, has advanced to become the most effective means for revascularization of stenosed vessels. In the early 1980's, angioplasty first became available for clinical practice in the coronary artery, and has since proven an effective alternative to conventional bypass graft surgery. Balloon catheter dependent angioplasty has consistently proven to be the most reliable and practical interventional procedure. Other ancillary technologies such as laser based treatment, or directional or rotational atherectomy, have proven to be either of limited effectiveness or dependent on balloon angioplasty for completion of the intended procedure. Restenosis following balloon-based angioplasty is the most serious drawback and is especially prevalent in the coronary artery system.

Many regimens have been designed to combat restenosis, with limited success, including laser based treatment and directional or rotational atherectomy. Intravascular stenting, however, noticeably reduces the restenosis rate following angioplasty procedures. The procedure for intravascular stent placement typically involves pre-dilation of the target vessel using balloon angioplasty, followed by deployment of the stent, and expansion of the stent such that the dilated vessel walls are supported from the inside.

The intravascular stent functions as scaffolding for the lumen of a vessel. The scaffolding of the vessel walls by the stent serve to: (a) prevent elastic recoil of the dilated vessel wall, (b) eliminate residual stenosis of the vessel; a common occurrence in balloon angioplasty procedures, (c) maintain the diameter of the stented vessel segment slightly larger than the native unobstructed vessel segments proximal and distal the stented segment and (d) as indicated by the latest clinical data, lower the restenosis rate. Following an angioplasty procedure, the restenosis rate of stented vessels has proven significantly lower than for not stented or otherwise treated vessels; treatments include drug therapy and other methods mentioned previously.

Another benefit of vessel stenting is the potential reduction of emergency bypass surgery arising from angioplasty procedures. Stenting has proven to be effective in some cases for treating impending closure of a vessel during angioplasty. Stenting can also control and stabilize an unstable local intimal tear of a vessel caused by normal conduct during an angioplasty procedure. In some cases, an incomplete or less than optimal dilatation of a vessel lesion with balloon angioplasty can successfully be opened up with a stent implant.

Early in its development, the practice of stenting, especially in coronary arteries, had serious anticoagulation problems. However, anticoagulation techniques have since been developed and are becoming simpler and more effective. Better and easier to use regimens are continuously being introduced, including simple outpatient anticoagulation treatments, resulting in reduced hospital stays for stent patients.

An example of a conventional stent patent is U.S. Pat. No. 5,102,417 (hereafter the Palmaz Patent). The stent described in the Palmaz Patent consists of a series of elongated tubular members having a plurality of slots disposed substantially parallel to the longitudinal axis of the tubular members. The tubular members are connected by at least one flexible connector member.

The unexpanded tubular members of the Palmaz Patent are overly rigid so that practical application is limited to short lengths. Even with implementation of the Multi-link design with flexible connector members connecting a series of tubular members, longer stents can not navigate tortuous blood vessels. Furthermore, the rigidity of the unexpanded stent increases the risk of damaging vessels during insertion. Foreshortening of the stent during insertion complicates accurate placement of the stent and reduces the area that can be covered by the expanded stent. There is, further, no method of programming the stent diameter along its longitudinal axis to achieve a tapered expanded stent, and no method of re-enforcement of stent ends or other regions is provided for.

Another example of a conventional stent patent is WO 96/03092, the Brun patent. The stent described in the Brun patent is formed of a tube having a patterned shape, which has first and second meander patterns. The even and odd first meander patterns are 180 degrees out of phase, with the odd patterns occurring between every two even patterns. The second meander patterns run perpendicular to the first meander patterns, along the axis of the tube.

Adjacent first meander patterns are connected by second meander patterns to form a generally uniform distributed pattern. The symmetrical arrangement with first and second meander patterns having sharp right angled bends allows for catching and snagging on the vessel wall during delivery. Furthermore, the large convolutions in the second meander pattern are not fully straightened out during expansion reducing rigidity and structural strength of the expanded stent. There is, further, no method of programming the stent diameter along its longitudinal axis to achieve a tapering stent design, and no method of re-enforcement of stent ends or other regions is provided for.

These and other conventional stent designs suffer in varying degrees from a variety of drawbacks including: (a) inability to negotiate bends in vessels due to columnar rigidity of the unexpanded stent; (b) lack of structural strength, axio-lateral, of the unexpanded stent; (c) significant foreshortening of the stent during expansion; (d) limited stent length; (e) constant expanded stent diameter; (f) poor crimping characteristics; and (g) rough surface modulation of the unexpanded stent.

There is a need for a stent with sufficient longitudinal flexibility in the unexpanded state to allow for navigation through tortuous vessels. There is a further need for a stent that is structurally strong in the unexpanded state such that risk of damage or distortion during delivery is minimal. A further need exists for a stent that maintains substantially the same longitudinal length during expansion to allow greater coverage at the target site and simplify proper placement of the stent. Yet a further need exists for a stent design with sufficient longitudinal flexibility that long stents of up to 100 mm can be safely delivered through tortuous vessels. There is a need for a stent that is configured to expand to variable diameters along its length, such that a taper can be achieved in the expanded stent to match the natural taper of the target vessel. A need exists for a stent which, (i) can be crimped tightly on the expansion balloon while maintaining a low profile and flexibility, (ii) has a smooth surface modulation when crimped over a delivery balloon, to prevent catching and snagging of the stent on the vessel wall during delivery or (iii) with re-enforcement rings on the ends or middle or both to keep the ends of the stent securely positioned against the vessel walls of the target blood vessel.

SUMMARY OF THE INVENTION

Accordingly an object of the present invention is to provide a scaffold for an interior lumen of a vessel.

Another object of the invention is to provide a stent which prevents recoil of the vessel following angioplasty.

A further object of the invention is to provide a stent that maintains a larger vessel lumen compared to the results obtained only with balloon angioplasty.

Yet another object of the invention is to provide a stent that reduces foreshortening of a stent length when expanded.

Another object of the invention is to provide a stent with increased flexibility when delivered to a selected site in a vessel.

A further object of the invention is to provide a stent with a low profile when crimped over a delivery balloon of a stent assembly.

Yet a further object of the invention is to provide a stent with reduced tuliping of a stent frame.

Another object of the invention is to provide a chain mesh stent that reduces vessel "hang up" in a tortuous vessel or a vessel with curvature.

A further object of the invention is to provide a chain mesh stent that increases radial and axio-lateral strength of the expanded stent.

These and other objectives of the invention are achieved in a stent in a non-expanded state. The stent of present invention is a 3-dimensional object with a generally tubular geometry, which includes inner and outer surface, inner and outer diameters, an internal tubular lumen, a wall thickness and a prescribed length. To describe the design geometry of the stent of present invention a cut open 2-dimensional illustrations are used extensively in this provisional application. Computer generated isometric and side elevation illustrations will be added in the formal application. Although description of the strut configurations of a tubular stent of present invention is according to 2-dimensional cut-open drawings, the real stent of present invention is a 3-dimensional tubular object designed to function as a scaffolding-device inside a blood vessel or an anatomic tubular structure of any kind in the body in which the stent can be implanted.

A first expansion column includes of a plurality of first expansion strut pairs of a generally horizontal arrangement. A first expansion strut pair includes a first expansion strut of a straight-line configuration that is in horizontal alignment adjacent to a second expansion strut of a straight-line configuration that is in horizontal alignment. A step down parallel notch is formed to allow a contralateral attachment of a diagonal connector strut at the distal end of a first expansion strut and proximal end of second expansion strut of a first expansion strut pair. A first joining strut couples the first and second expansion struts at a distal end of the first expansion strut pair to form a closed loop. A second expansion strut pair includes a third expansion strut of a straight-line configuration that is in horizontal alignment adjacent to a second expansion strut of a straight-line configuration that is in horizontal alignment. A step down parallel notch is formed to allow a contralateral attachment of a diagonal connector strut at a distal end of a third expansion strut of a second expansion-strut pair. A second joining strut couples the second and third expansion struts at a proximal end of the second expansion strut pair to form a closed loop. A third expansion strut pair includes a fourth expansion strut of a straight-line configuration that is in horizontal alignment adjacent to a third expansion strut of a straight-line configuration that is in horizontal alignment. A step down parallel notch is formed to allow a contralateral attachment of a diagonal connector strut at the distal end of a fourth expansion strut of a third expansion strut pair. A third joining strut couples the third and fourth expansion struts at a distal end of the third expansion strut pair to form a closed loop. A fourth expansion strut pair includes a fifth expansion strut of a straight-line configuration that is in horizontal, alignment adjacent to a fourth expansion strut of strut of a straight-line configuration that is in horizontal alignment. A step down parallel notch is formed to allow a contralateral attachment of a diagonal connector strut at a distal end of a fifth expansion strut. A fourth joining strut couples the fourth and fifth expansion struts at a proximal end of a fourth expansion-strut pair to form a closed loop. There are twelve (12) closed loop expansion strut pairs in the main figures of this application formed by a step by step construction of each expansion strut pairs in sequence.

An expansion strut pair includes two companion straight-line expansion-struts and a joining strut to form a closed or blind loop at a proximal or distal end. This expansion strut pair loop construction can be repeated to make the prescribed number of expansion strut pairs around the circumference in an unbroken fashion in a first expansion column of a tubular stent of present invention. A set of two consecutive closed loop expansion strut pairs in sequence in an expansion column is called an expansion strut pair cycle. In this provisional application, the illustrations would contain 12 expansion strut pairs making 6 expansion strut pair cycles in a first expansion column in the cut-open 2-dimensional drawings. Each expansion strut pair cycle would have one closed loop pointing proximally and one closed loop pointing distally. Of the twelve (12) expansion strut pairs in a first expansion column, therefor, one half of expansion strut pair closed loops point proximally and one half of expansion strut pair closed loops point distally. Although there are six (6) expansion strut pair cycles in the main illustrations of this provisional application, the number of expansion strut pair cycles can variably be changed according to a prescribed requirement of a specific stent made. This variability of having a more or less than twelve expansion-strut pairs in an expansion column is within the scope of a tubular stent of present invention.

At least one of the two companion expansion struts of a first expansion strut pair has a step-down or step-up parallel notch for contralateral attachment of a diagonal connector. However, a contralateral attachment of a diagonal connector can be achieved without a step-down or step-up horizontal notch on a first or second expansion strut of a first, second, third or fourth expansion strut pairs, etc., in a first expansion column. The variation of presence or absence of the step-down or step-up parallel notch for contralateral attachment of a diagonal connector in any first or second expansion strut of any expansion strut pair in any expansion strut column is within the scope of a tubular stent of the present invention.

The first and second expansion struts of horizontal alignment in a first expansion strut pair in a first expansion column parallel to each other. But the first and second expansion struts in a first expansion strut pair in a first expansion column may not parallel to each other. A first or second expansion strut of a first expansion strut pair in a first expansion column may parallel to the longitudinal axis of the tubular stent. These parallel or non-parallel strut arrangement variations in any strut pair in any expansion column are within the scope of a tubular stent of the present invention.

A first expansion strut pair first corner is formed where the first joining strut is coupled to the first expansion strut, and a first expansion strut pair second corner is formed where the first joining strut is coupled to the second expansion strut. A second expansion strut pair first corner is formed where the second joining strut is coupled to the second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut. All the expansion strut pairs in a first expansion column are joined with their respective joining struts.

A second expansion column includes of a plurality of closed loop second expansion strut pairs of straight-line configuration in generally horizontal arrangement. A first expansion strut pair in a second expansion column includes a first expansion strut of horizontal alignment adjacent to a second expansion strut of horizontal alignment. A step-up parallel notch is formed to allow a contralateral attachment of a diagonal connector strut at the distal end of a first expansion strut and a similar step-up parallel notch in the proximal end of a second expansion strut of a first expansion strut pair. A first joining strut couples the first and second expansion struts at a proximal end of a first expansion strut pair to form a closed loop. A second expansion strut pair in a second expansion column includes a third expansion strut of horizontal alignment adjacent to a second expansion strut of horizontal alignment. A step-up parallel notch is formed to allow a contralateral attachment of a diagonal connector strut at the distal end of a third expansion strut of a second expansion strut pair. A second joining strut couples the second and third expansion struts at a distal end of a second expansion strut pair to form a closed loop. A third expansion strut pair in second expansion column includes a fourth expansion strut of horizontal alignment adjacent to a third expansion strut of horizontal alignment. A step up parallel notch is formed to allow a contralateral attachment of a diagonal connector strut at the proximal end of a fourth expansion strut of a third expansion strut pair. A third joining strut couples the third and fourth expansion struts at a proximal end of a third expansion strut pair to form a closed loop. A fourth expansion strut pair in a second expansion column includes a fifth expansion strut of horizontal alignment adjacent to a fourth expansion strut of horizontal alignment. A step up parallel notch is formed to allow a contralateral attachment of a diagonal connector strut at a distal end of a fifth expansion strut of a fourth expansion strut pair. A fourth joining strut couples the fourth and fifth expansion struts at a distal end of a fourth expansion strut pair to form a closed loop. There are twelve (12) closed loop expansion strut pairs in the main figures of this application formed by a step by step construction of each expansion strut pairs in sequence.

An expansion strut pair includes two companion straight-line expansion-struts and a joining strut to form a closed or blind loop at a proximal or distal end. This expansion strut pair loop construction can be repeated to make the prescribed number of expansion strut pairs around the circumference in an unbroken fashion in a first expansion column of a tubular stent of present invention. A set of two consecutive closed loop expansion strut pairs in sequence in an expansion column is called an expansion strut pair cycle. In this provisional application, the illustrations would contain 12 expansion strut pairs making 6 expansion strut pair cycles in a first expansion column in the cut-open 2-dimensional drawings. Each expansion strut pair cycle would have one closed loop pointing proximally and one closed loop pointing distally. Of the twelve (12) expansion strut pairs in a first expansion column, therefor, one half of expansion strut pair closed loops point proximally and one half of expansion strut pair closed loops point distally. Although there are six (6) expansion strut pair cycles in the main illustrations of this provisional application, the number of expansion strut pair cycles can variably be changed according to a prescribed requirement of a specific stent made. This variability of having a more or less than twelve (12) expansion-strut pairs in an expansion column is within the scope of a tubular stent of present invention.

In this provisional application, at least one of the two companion expansion struts of a first expansion strut pair has a step-down or step-up parallel notch for contralateral attachment of a diagonal connector. However, a contralateral attachment of a diagonal connector can be achieved without a step-down or step-up horizontal notch on a first or second expansion strut of a first, second, third or fourth expansion strut pairs, etc., in a second expansion strut column. The variation of presence or absence of the step-down or step-up parallel notch for contralateral attachment of a diagonal connector in any first or second expansion strut of any expansion strut pair in any expansion strut column is within the scope of a tubular stent of the present invention.

The first and second expansion struts of horizontal alignment in a first expansion strut pair in a second expansion column parallel to each other. But the first and second expansion struts in a first expansion strut pair in a second expansion column may not parallel to each other. A first or second expansion strut of a first expansion strut pair in a second expansion column may parallel to the longitudinal axis of the tubular stent. These parallel or non-parallel strut alignment variations in any strut pair in any expansion column are within the scope of a tubular stent of the present invention.

In a second expansion column, a first expansion strut pair first corner is formed where the first joining strut is coupled to a first expansion strut, and a first expansion strut pair second corner is formed where the first joining strut is coupled to the second expansion strut. Likewise, a second expansion strut pair first corner is formed where the second joining strut is coupled to a second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut. All the expansion strut pairs in a second expansion column are joined with their respective joining struts.

A first connecting strut column is formed of a plurality of first connecting struts. Each connecting strut of a first connecting strut column includes a connecting strut proximal section, a connecting strut distal section and a connecting strut intermediate section. A first connecting strut proximal section has two parts: a short part and a long part. A first connecting strut proximal section short part is coupled at a perpendicular or slant angle to the contralateral out side of the distal parallel notch in the distal end of a first expansion strut of a first expansion strut pair of a first expansion column. A first connecting strut proximal section long part is coupled to the short part proximally at a generally perpendicular or a slant angle and to the intermediate section distally. The proximal long part generally parallels to the longitudinal axis of a first expansion strut of a first expansion strut pair of a first expansion column. However, the proximal long part can be made not to parallel to the longitudinal axis of a first expansion strut of first expansion strut pair of first expansion column. A first connecting strut distal section also has two parts: a short part and a long part. A first connecting strut distal section short part is coupled at a perpendicular or slant angle to the contralateral out side of the proximal parallel notch in the proximal end of a second expansion strut of a first expansion strut pair of a second expansion column. A distal long part is coupled to the short part distally at a generally perpendicular or a slant angle and to the intermediate section proximally. The distal long part generally parallels to the longitudinal axis of a first expansion strut of a first expansion strut pair of a second expansion column. However, the distal long part can be made not to parallel to the longitudinal axis of a first expansion strut of first expansion strut pair of a second expansion column. A first connecting strut proximal section and a first connecting strut distal section are mirror mages to each other. The proximal and distal end of a first-connecting strut pointed to opposite directions or different directions. A first connecting strut intermediate section proximal end is coupled at a slant angle to the distal end of first connecting strut proximal section and a first connecting strut intermediate section distal end is coupled at a slant angle to the proximal end of a first connecting strut distal section. The intermediate section of a first connecting strut traverses through the inter-connecting space separating the first joining strut of a first expansion strut pair in a first expansion strut column and the first joining strut of a first expansion strut pair in a second expansion strut column.

A second, third, or fourth connecting strut in a first connecting strut column has identical connecting strut configuration like a first connecting strut in a first connecting strut column as described in the foregoing paragraph. Each of a second, third or fourth connecting strut in a first connecting column connects a first expansion column to a second expansion column at their respective coupling locations to make a full and unbroken ring of connecting column around the circumference of a tubular stent of the present invention. A second connecting strut, in a similar manner as a first connecting strut described above, connects a second expansion strut pair in a first expansion column to a second expansion strut pair in a second expansion column. A third connecting strut connects a third expansion strut pair in a first expansion column to a third expansion strut pair in a second expansion column. A fourth connecting strut connects a fourth expansion strut pair in a first expansion column to a fourth expansion strut pair in a second expansion column. Likewise, a fifth connecting strut, a sixth connecting strut, etc. connects a fifth expansion strut pair, a sixth expansion strut pair, etc. of a first expansion column to a fifth expansion strut pair, a sixth expansion strut pair, etc. of a second expansion column respectively.

A third expansion column includes of a plurality of third expansion strut pairs of straight-line configuration in a generally horizontal arrangement. A first expansion strut pair in a third expansion column includes a first expansion strut of horizontal alignment adjacent to a second expansion strut of horizontal alignment. A step-down parallel notch is formed to allow a contralateral attachment of a diagonal connector strut at a distal end of a first expansion strut and a similar step-down parallel notch in a proximal end of a second expansion strut of a first expansion strut pair. A first joining strut couples the first and second expansion struts at a distal end of a first expansion strut pair to form a closed loop. A second expansion strut pair in a third expansion column includes a third expansion strut of horizontal alignment adjacent to a second expansion strut of horizontal alignment. A step-down parallel notch is formed to allow a contralateral attachment of a diagonal connector strut at a distal end of a third expansion strut of a second expansion strut pair. A second joining strut couples the second and third expansion struts at a proximal end of a second expansion strut pair to form a closed loop. A third expansion strut pair in a third expansion column includes a fourth expansion strut of horizontal alignment adjacent to a third expansion strut of horizontal alignment. A step-down parallel notch is formed to allow a contralateral attachment of a diagonal connector strut at a proximal end of a fourth expansion strut of a third expansion strut pair. A third joining strut couples the third and fourth expansion struts at a distal end of a third expansion strut pair to form a closed loop. A fourth expansion strut pair in a third expansion column includes a fifth expansion strut of horizontal alignment adjacent to a fourth expansion strut of horizontal alignment. A step-down parallel notch is formed to allow a contralateral attachment of a diagonal connector strut at a distal end of a fifth expansion strut of a fourth expansion strut pair. A fourth joining strut couples the fourth and fifth expansion struts at a proximal end of a fourth expansion strut pair to form a closed loop. There are twelve (12) closed loop expansion strut pairs in the main figures of this application formed by a step by step construction of each consecutive expansion strut pairs in sequence.

An expansion strut pair includes two companion straight-line expansion-struts and a joining strut to form a closed or blind loop at a proximal or distal end. This expansion strut pair loop construction can be repeated to make the prescribed number of expansion strut pairs around the circumference in an unbroken fashion in a first expansion column of a tubular stent of present invention. A set of two consecutive closed loop expansion strut pairs in sequence in an expansion column is called an expansion strut pair cycle. In this provisional application, the illustrations would contain 12 expansion strut pairs making 6 expansion strut pair cycles in a first expansion column in the cut-open 2-dimensional drawings. Each expansion strut pair cycle would have one closed loop pointing proximally and one closed loop pointing distally. Of twelve (12) expansion strut pairs in first expansion column, therefor, one half of expansion strut pair closed loops point proximally and one half of expansion strut pair closed loops point distally. Although there are six (6) expansion strut pair cycles in the main illustrations of this provisional application, the number of expansion strut pair cycles can variably be changed according to a prescribed requirement of a specific stent made. This variability of having a more or less than twelve expansion-strut pairs in an expansion column is within the scope of a tubular stent of present invention.

In the stent strut configuration, at least one of the two companion expansion struts of a first expansion strut pair has a step-down or step-up parallel notch for contralateral attachment of a diagonal connector. However, a contralateral attachment of a diagonal connector can be achieved without a step-down or step-up horizontal notch on a first or second expansion strut of a first, second, third or fourth expansion strut pairs, etc., in a first expansion strut column. The variation of presence or absence of the step-down or step-up parallel notch for contralateral attachment of a diagonal connector in any first or second expansion strut of any expansion strut pair in any expansion strut column is within the scope of a tubular stent of the present invention.

The first and second expansion struts of horizontal alignment in a first expansion strut pair in a third expansion column parallel to each other. But the first and second expansion struts in a first expansion strut pair in a first expansion strut column may not parallel to each other. A first or second expansion struts of a first expansion strut pair in a first expansion column may parallel to the longitudinal axis of the tubular stent. These parallel or non-parallel strut arrangement variations in any strut pair in any expansion column are within the scope of a tubular stent of the present invention.

In a third expansion column, a first expansion strut pair first corner is formed where the first joining strut is coupled to a first expansion strut, and a first expansion strut pair second corner is formed where the first joining strut is coupled to the second expansion strut. Likewise, a second expansion strut pair first corner is formed where the second joining strut is coupled to a second expansion strut, and a second expansion strut pair second corner is formed where the second joining strut is coupled to the third expansion strut. A third expansion strut pair first corner is formed where the third joining strut is coupled to the third expansion strut, and a third expansion strut pair second corner is formed where the third joining strut is coupled to the fourth expansion strut. A fourth expansion strut pair first corner is formed where the fourth joining strut is coupled to the fourth expansion strut, and a fourth expansion strut pair second corner is formed where the fourth joining strut is coupled to the fifth expansion strut. All the expansion strut pairs in a third expansion column are joined with their respective joining struts.

A second connecting strut column is formed of a plurality of second connecting struts, each connecting strut of a second connecting strut column includes a connecting strut proximal section, a connecting strut distal section and a connecting strut intermediate section. The proximal section of a first connecting strut in a second connecting strut column has two parts: a short part and a long part. The short part is coupled at a perpendicular or slant angle to the contralateral out side of the distal parallel notch in the distal end of a third expansion strut of a second expansion strut pair of a second expansion column. The long part is coupled to the short part proximally at a generally perpendicular or a slant angle and to the intermediate section distally. The long part generally parallels to the longitudinal axis of a distal half of a third expansion strut of a second expansion strut pair of a second expansion column. However, the long part can be made not to parallel to the longitudinal axis of a distal half of a third expansion strut of second expansion strut pair of second expansion column. A first connecting strut distal section has two parts: a short part and a long part. The short part is coupled at a perpendicular or slant angle to the contralateral out side of the proximal parallel notch in the proximal end of a second expansion strut of a second expansion strut pair of a third expansion column. A long part is coupled to the short part distally at a generally perpendicular or a slant angle and to the intermediate section proximally. The long part generally parallels to the longitudinal axis of a proximal half of a second expansion strut of a second expansion strut pair of a third expansion column. However, the long part can be made not to parallel to the longitudinal axis of a proximal half of a second expansion strut of second expansion strut pair of a third expansion column. In a second connecting strut column, a first connecting strut proximal section and a first connecting strut distal section are irror images to each other, and with their ends pointing to opposite or different directions. A first connecting strut intermediate section proximal end is coupled at a slant angle to the distal end of first connecting strut proximal section and a first connecting strut intermediate section distal end is coupled at a slant angle to the proximal end of a first connecting strut distal section. The intermediate section of a first connecting strut traverses through the inter-connecting space separating the first joining strut of a second expansion strut pair in a second expansion strut column proximally and the second joining strut of a second expansion strut pair in a third expansion strut column. The orientation of a first connecting strut in a second connecting strut column is a mirror image if the orientation of a first connecting strut in a first connecting strut column.

A second, third, or fourth connecting strut in a second connecting strut column has identical connecting strut configuration as a first connecting strut in a second connecting strut column as described in the foregoing paragraph. Each of a second, third or fourth connecting strut in a second connecting column connects a second expansion column to a third expansion column at their respective coupling locations to make a full and unbroken ring of connecting column around the circumference of a tubular stent of the present invention. A second connecting strut in a second connecting strut column, in a similar manner as a first connecting strut described above, connects a fourth expansion strut pair in a second expansion column to a fourth expansion strut pair in a third expansion column. A third connecting strut in a second connecting strut column connects a sixth expansion strut pair in a second expansion column to a sixth expansion strut pair in a third expansion column. A fourth connecting strut in a second connecting strut column connects an eighth expansion strut pair in a second expansion column to an eighth expansion strut pair in a third expansion column. Likewise, a fifth connecting strut, a sixth connecting strut, etc. connects a tenth expansion strut pair, a twelfth expansion strut pair, etc. of a second expansion column to a tenth expansion strut pair, a twelfth expansion strut pair, etc. of a third expansion column respectively.

BRIEF DESCRIPTION OF THE DRAWINGS

FIG. 4b—A magnified view of the unexpanded 2-dimensional cut-open stent 10 detailing an alternative contralateral coupling pattern of the proximal 66 and distal 70 stems, of the connecting strut 44 to the sides 43 of the straight portions, opposite from the stepped parallel notches 50 and 52, with longitudinal axes 58 of the expansion struts 42.

DETAILED DESCRIPTION OF THE DRAWINGS

Figure 1:
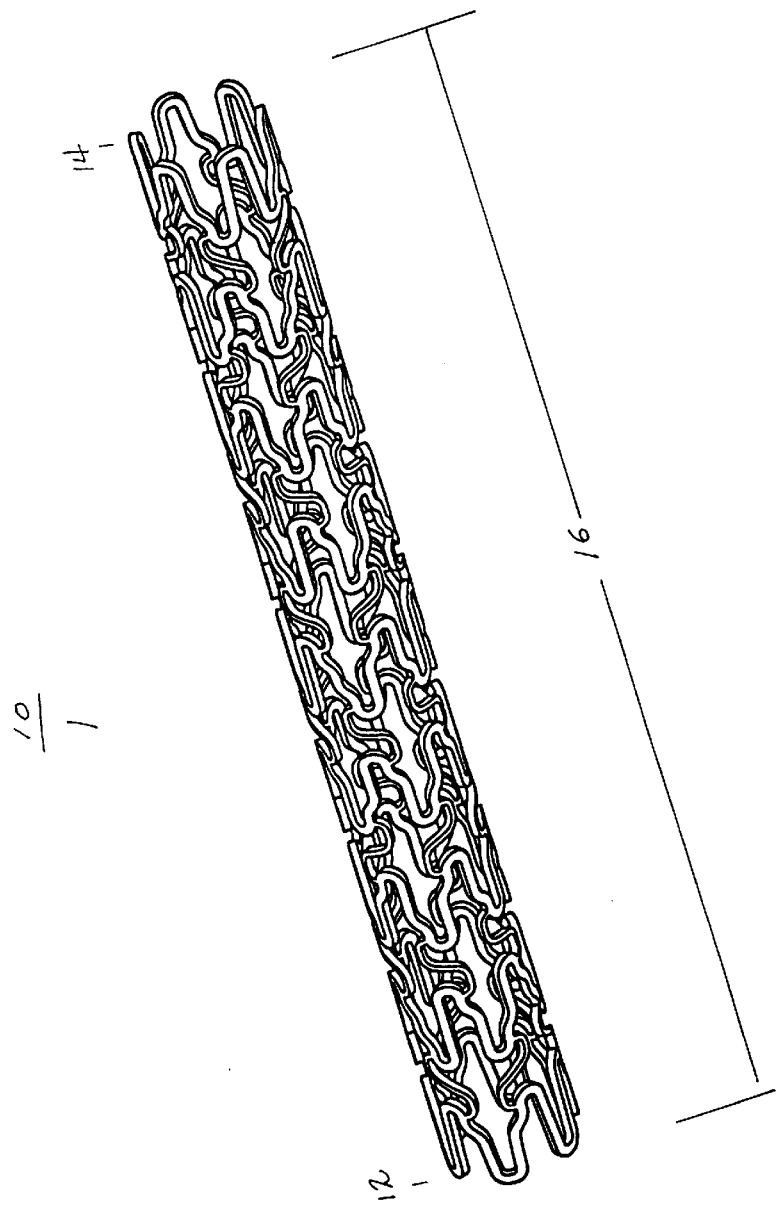
FIG. 1—A tubular unexpanded the stent 10 of present invention in a computer-generated isometric drawing.

FIG. 1 presents a tubular shaped vascular stent 10 of present invention in a CAD isometric drawing in scale. The stent 10 has a tubular shape with combination of the expansion struts and connector struts in a continuous chain-mesh pattern for best possible vessel coverage when expanded inside of a vessel or a tubular organ structure. The unique connector design of the stent 10 gives excellent flexibility during delivery phase with very smooth external and internal surface modulations. The connector 44 configuration also has minimal foreshortening when expanded. The stent 10 has a proximal end 12 with a proximal opening and a distal end 14 with a distal opening for the inner lumen of the stent 10, which will passively enlarge in internal diameter when expanded. The length 16 of the stent 10 is defined by the longitudinal axis 17 between the proximal end 12 and the distal end 14.

Figure 2:
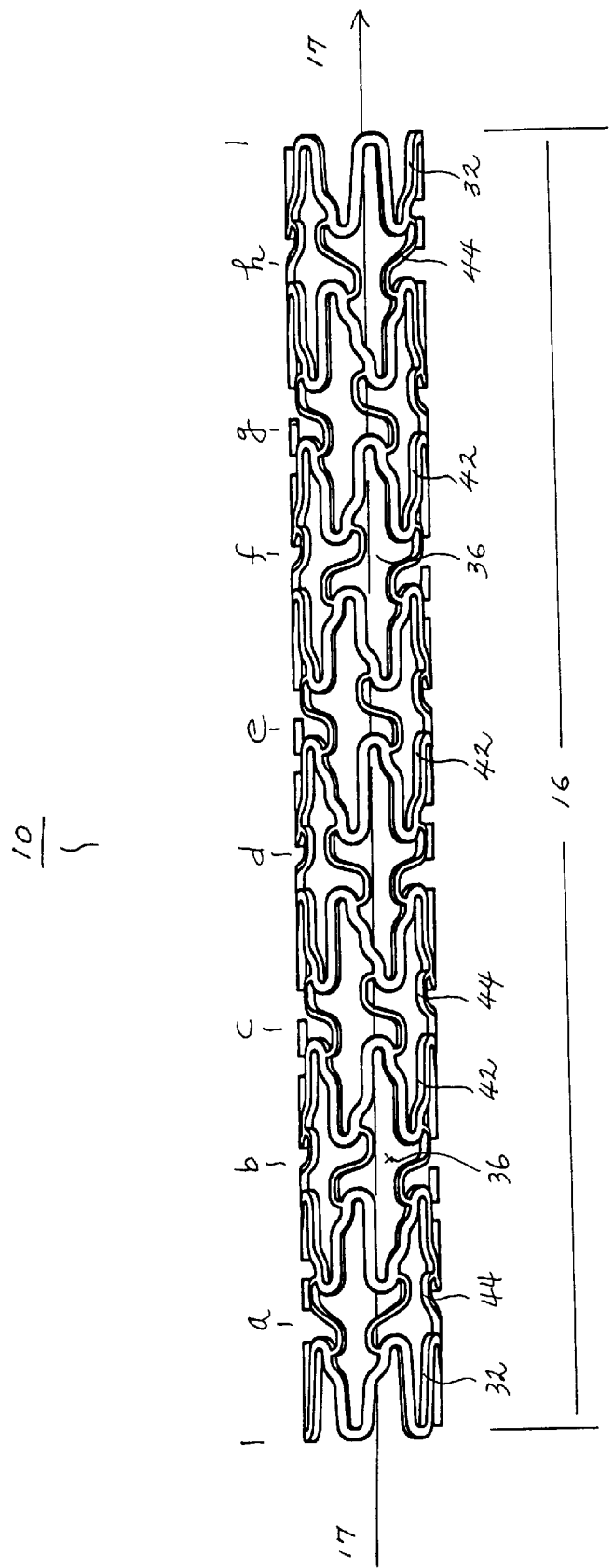
FIG. 2—A side elevation of a variation of stent 10 of present invention demonstrating the front half of the stent strut features.

FIG. 2 is a side elevation of the stent 10 in a scale CAD drawing of the same stent 10 depicted in isometric view of FIG. 1. This CAD diagram illustrates the details of the expansion struts 42, the connecting struts 44 and the stent cells 36. Counting from left to right, the connecting struts 44 in the first (1), the fourth (4) and the eighth (8) inter-expansion-strut spaces are arranged in a symmetrical pattern in the longitudinal plane of the stent 10. In the first inter-expansion-strut space (a), the closely paired proximal portions 68 of the two adjacent connector struts 44 have their proximal stems 66 pointing away from each other as the proximal stems 66 join to their respective attachment sites at the sides of distal ends of the expansion strut 42 pairs on the left; and the distal stems 70 of the distal portions 72 of the two paired connecting struts 44 are widely separated with their distal stems 70 pointing toward each other as the distal stems 70 join to their respective attachment sites at the sides of proximal ends of the expansion strut 42 pairs on the right. In the same inter-expansion-strut space (a), the proximal stem 66 of a third connecting strut 44, adjacent to the two closely paired proximal stems 66 discussed above, is widely separated pointing its proximal stem 66 toward the adjacent closely paired proximal stems 66; while the distal stem 70 of the distal portion 72 of a third connector strut 44 is now closely paired with the distal stem of adjacent connector 44 pointing their distal stems 70 pointing way from each other as their distal stems 70 join to their respective coupling site on the sides of proximal ends of the expansion strut 42 pair on the right. This alternating pattern of closely or widely pairing of the two adjacent proximal 68 or distal 72 portions of the two adjacent connecting struts 44 with their respective proximal 66 or distal 70 stems continues around the circumference of the stent 10. There are 6 connecting struts 44 in the inter-expansion-strut spaces (a) around the circumference of the stent 10 of FIG. 2. With six (6) connectors arranged in an alternating (symmetrical) close or wide pairing pattern of the proximal 68 portion and distal portion 72 of the connector struts 44, the space between the two adjacent connectors is evenly distributed and perpetually repeats around the circumference of the stent 10. This close or wide pairing pattern of two adjacent connectors 44 in the inter-expansion-strut-space (a) repeats in the inter-expansion-strut spaces of (d) and (h) of the stent 10 of FIG. 2. Other possible variations of similar connector arrangement pattern are also within the scope of stent 10 of present invention.

Figure 3:
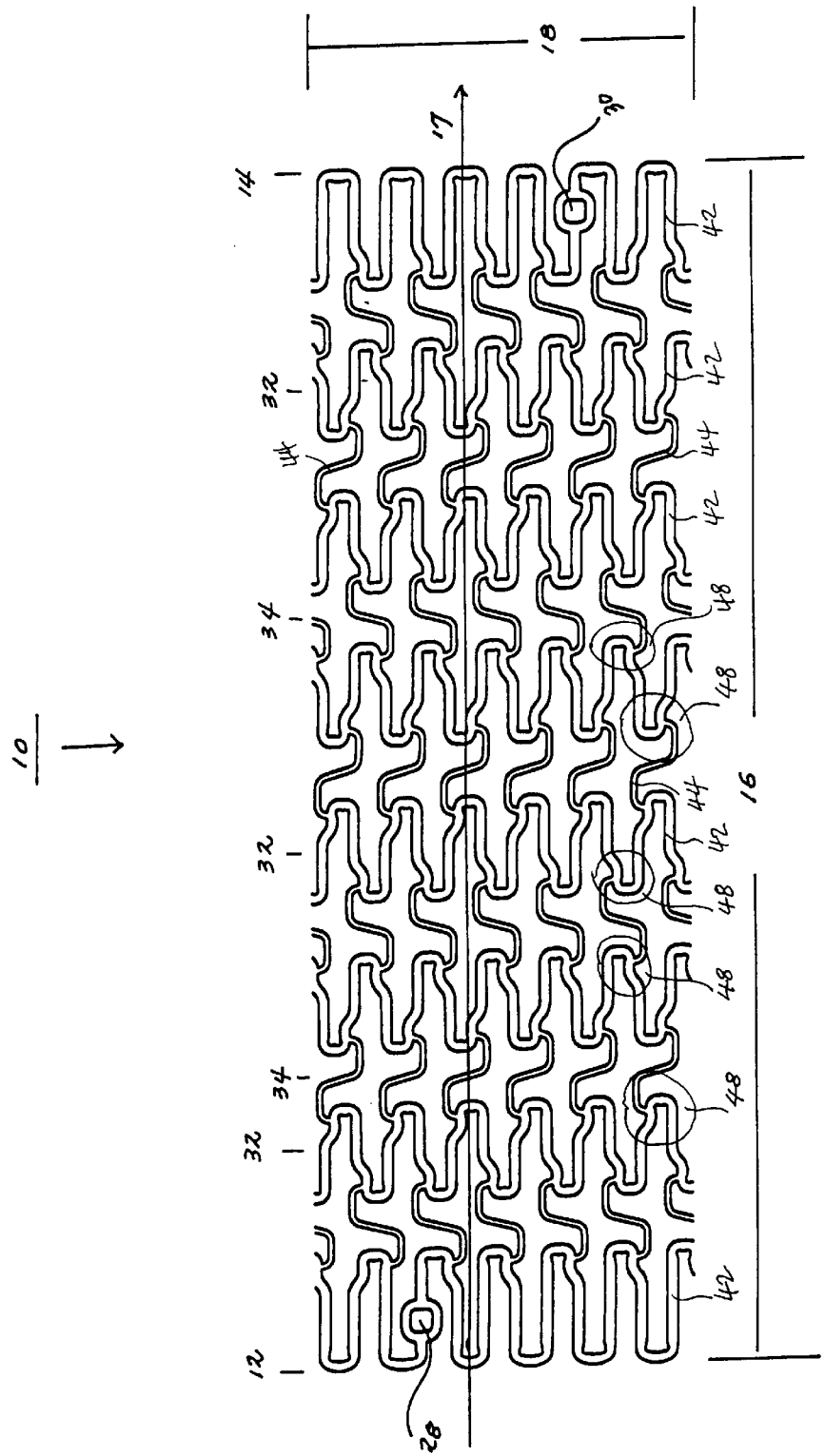
FIG. 3—A 2-dimensional cut-open view of the stent 10 of present invention illustrating the design features of strut pattern FIG. 4—A magnified view of the unexpanded 2-dimensional cut-open stent 10 detailing the expansion columns 32 and the connector columns 34.
Figure 4:
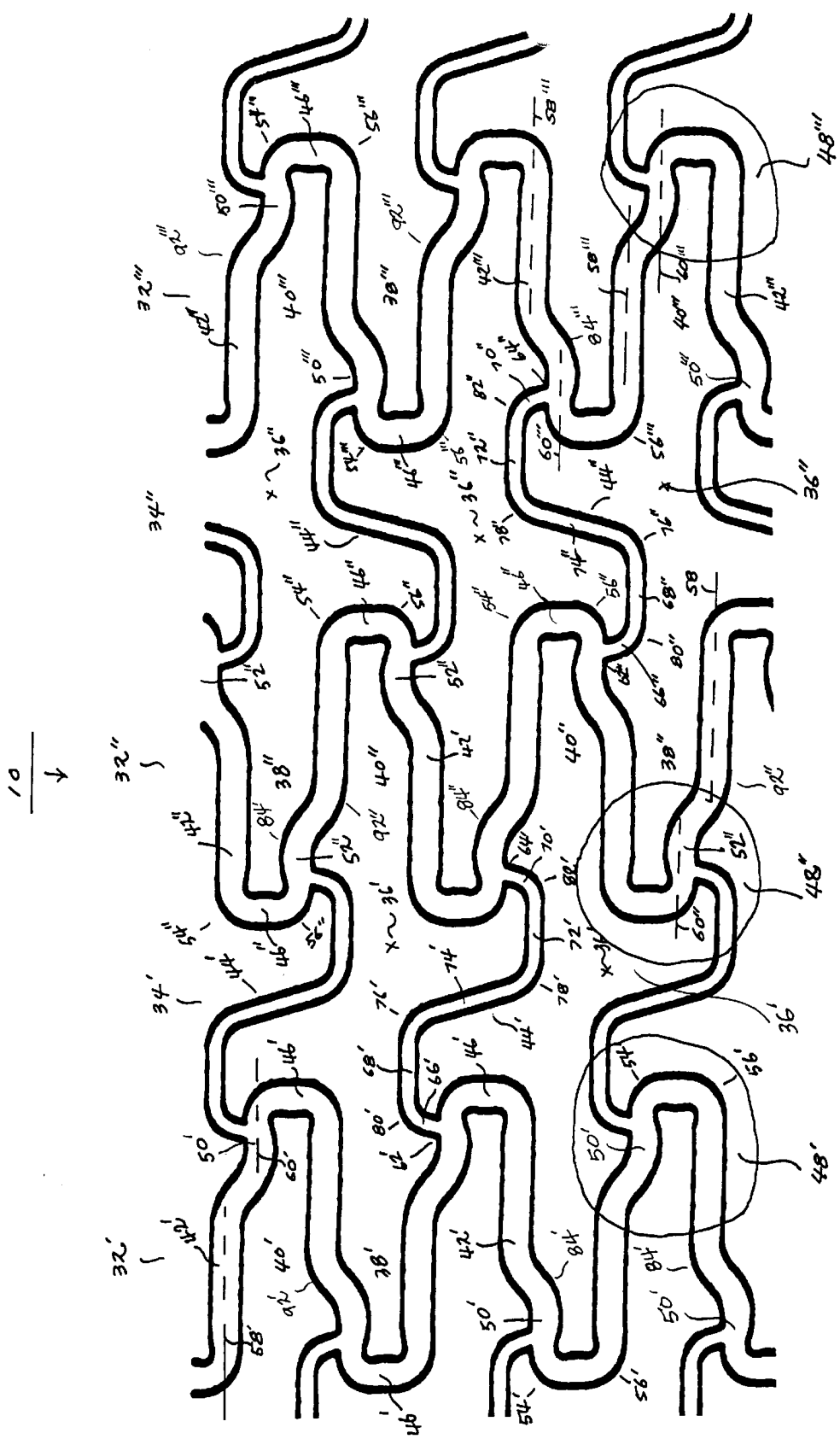

In the other Inter-expansion-strut spaces (b), (c), (e), (f) and (g) of FIG. 2 has connector arrangement pattern similar to the pattern disclosed in FIGS. 3 and 4.

FIG. 3 illustrates an unexpanded tubular stent 10 of present invention in this 2-dimensional cut open drawing. However, the stent 10 is a 3-dimensional tubular structure in reality similar to the stent 10 illustrated in FIGS. 1 & 2, but 2-dimensional drawings are extensively used to easily illustrate the key structural and design features of the stent 10.

In this illustration, the proximal end 12 of the stent 10 is on the left side and the distal end 14 is on the right. The cut-open stent 10 is laid out with the length 16 and longitudinal axis 17 of the stent 10 horizontally aligned. The circumference 18 of the stent 10 is on a vertical plane. There are eight (8) expansion columns 32 connected by seven (7) connector columns 34, in an unbroken chain-mesh around the circumference 18 and along the length 16, creating a tubular structure with longitudinal axis 17 aligned horizontally. Both the first and last expansion columns have their respective marker buttons 28 and 30 in their columns. The marker buttons 28 and 30 can be filled with a high density metal, such as gold, for a radiopaque marking.

FIG. 4 is a magnified view of FIG. 3 to add more detailed markers to the figure. An individual expansion strut 42 in an expansion strut pair in an expansion column 32 is aligned horizontally so that a longitudinal axis 58 of an expansion strut 42 of an expansion strut pair in an expansion column 32 would parallel to the longitudinal axis 17 of a tubular stent 10.

A first expansion column 32' of stent 10 is made of a plurality of two adjacent companion expansion struts 42' of horizontal alignment and a joining strut 46' to form a closed loop slot 48' at a proximal or distal end of an expansion strut 42' pair. A joining strut 46' forms a first corner 54' where the joining strut 46' joins a first expansion strut 42' and a second corner 56' is formed where the joining strut 46' joins a second expansion strut 42' of a first expansion strut 42' pair. A proximal cell slot 38' or a distal cell slot 40' is formed inside a closed loop 48' of an expansion strut 42' pair in a first expansion column 32'. An expansion strut 42' in a first expansion column 32' is aligned horizontally, generally paralleling to the longitudinal axis 17 of the stent 10. Also first and second adjacent expansion struts 42' in a first expansion column 32' are aligned horizontally so that first and second expansion strut 42' would parallel to each other. However, one of the two expansion strut 42' in an expansion strut 42' pair in a first expansion column 32' may not parallel to the longitudinal axis 17 of the stent 10 or to the adjacent companion expansion strut 42'. An expansion strut 42' pair in a first expansion column 32' has a stepped-down parallel notch 50' outside on a distal or proximal end of an expansion strut 42' pair near the closed loop 48' and apart from a joining strut 46'. A stepped-down parallel notch 50' is created to make it an attachment site an end of diagonal connector 44' in a contralateral position from the attachment position of the other end of the same connector 44'. A longitudinal axis 60' of a stepped-down parallel notch 50' or a stepped-up parallel notch 52" parallels to a longitudinal axis 58' of an expansion strut 42'. In FIGS. 3 and 4, a first expansion column 32' has twelve (12) closed loop 48' expansion strut 42' pairs in an unbroken fashion around the circumference 18 of the stent 10. Out of twelve (12) expansion strut 42' pairs, six (6) of them have their closed loop 48' pointed proximally and the other six (6) have their closed loops 48' pointed distally in an alternating sequence. Therefor, each expansion strut 42' is connected to a closed loop 48' on each end. One closed loop 48' on one end of an expansion strut 42' points distally and other closed loop 48' on the other end points proximally. The twelve (12) expansion strut 42' pair closed loops 48' in a first expansion column 32', therefor, make a set of six (6) expansion strut 42' pair cycles; with each expansion strut 42' pair cycle consists of two (2) closed loop 48' and two expansion struts 42'. All the corners or angled areas in a first expansion column 32' has their respective radius of curvature to minimize sharp corners as follows: a radius of curvature at a first corner 54', a radius of curvature at a second corner 56', a radius of curvature at a inner side of first corner 54', a radius of curvature at a inner side of second corner 56', a radius of curvature 92' at an outer edge of a stepped-parallel notch and a radius of curvature 84' at a inner edge of a stepped-parallel notch.

A second expansion column 32" of stent 10 is made of a plurality of two adjacent companion expansion struts 42" and a joining strut 46" to form a proximal or distal end of an expansion strut 42" pair to form a closed loop slots 38" or 40". A joining strut 46" forms a first corner 54" where the joining strut 46" joins a first expansion strut 42" and a second corner 56" where the joining strut 46" joins a second expansion strut 42" in a second expansion column 32". A closed loop 48' of an expansion strut 42' pair in a second expansion column 32" form a proximal cell slot 38" or a distal cell slot 40" inside a closed loop 48" of an expansion strut 42' pair. An expansion strut 42" in a second expansion column 32" is aligned horizontally to generally parallel to the longitudinal axis 17 of the stent 10. Also first and second adjacent companion expansion strut 42" in a second expansion column 32" are aligned horizontally so that first and second expansion strut 42" may parallel to each other. However, one of the two expansion struts 42" in an expansion strut 42" pair in a second expansion column 32" may not parallel to the longitudinal axis 17 of the stent 10 or may not parallel to its companion expansion strut 42". An expansion strut 42" pair in a second expansion column 32" has a stepped-up parallel notch 52" outside on a proximal or distal end of an expansion strut 42" pair near the closed loop 48" and apart from joining strut 46". A stepped-up parallel notch 52" is created to accommodate attachment of a distal stem 70' of a first connecting strut 44' in a contralateral position in relation to the attachment position of a proximal stem 66' of the same connecting strut 44'. A longitudinal axis 60" of a stepped-up parallel notch 52" of a second expansion strut 42" parallels to a longitudinal axis 58" of an expansion strut 42". In FIGS. 3 and 4 of this application, a second expansion column 32" has twelve (12) closed loops 48" of expansion strut 42' pairs in an unbroken fashion around the circumference 18 of the stent 10. Out of twelve (12) expansion strut 42" pairs, six (6) of them have their closed loop 48" pointed distally and the other six (6) closed loops 48" pointed proximally in an alternating sequence. Therefor, each expansion strut 42" is connected to a closed loop 48" on each end of an expansion strut 42". One closed loop 48" is connected to the proximal end and other closed loop 48" to the distal end. The twelve (12) expansion strut closed loops 46" in a second expansion column 32", therefor, make a set of six (6) expansion strut 42" pair cycles; with each expansion strut 42" pair cycle consists of two closed loops 48" and two expansion struts 42". All the corners or angled areas in a second expansion column 32" have a radius of curvatures to minimize sharp edges in their respective sharp angled or corner areas as follows: a radius of curvature at a first corner 54", a radius of curvature at a second corner 56", a radius of curvature at a inner side of first corner 54", a radius of curvature at a inner side of second corner 56", a radius of curvature 92" at an outer edge of a stepped-parallel notch and a radius of curvature 84" at a inner edge of a stepped-parallel notch.

A first connecting column 34' is formed of a plurality of first connecting strut 44'. Each connecting strut 44' in a first connecting strut column 34' includes a connecting strut proximal section with a proximal stem 66', a connecting strut distal section with a distal stem 70' and a connecting strut intermediate section 74'. A first connecting strut proximal section has two parts: a short stem 66' and a long portion 68'. A first connecting strut proximal section proximal end 62' of the short stem 66' is coupled at a perpendicular or slant angle to the contralateral outside of the distal parallel stepped notch 50' in the distal end of a first expansion strut 42' of a first expansion strut pair of a first expansion column 32'. A first connecting strut proximal section long portion 68' is coupled to the short stem 66' proximally at a junction 80' and to the intermediate section 74' distally at a junction 76'. The proximal long part 68' generally parallels to the longitudinal axis 58' of a first expansion strut 42' of a first expansion strut 42' pair in a first expansion column 32'. However, the proximal long part 68' can be made not to parallel to the longitudinal axis 58' of a first expansion strut 42" of first expansion strut 42' pair in a first expansion column 32'. A first connecting strut distal section also has two parts: a short stem stem 70' and a long part 72'. A first connecting strut distal end 64' of distal section short stem 70' is coupled at a perpendicular or slant angle to the contralateral out side of the proximal stepped parallel notch 52' in a proximal end of a second expansion strut 42" of a first expansion strut 42" pair in a second expansion column 32". A distal long portion 72' is coupled to the short stem 70' distally at a junction 82' at a generally perpendicular or a slant angle and to the intermediate section 74' proximally at a junction 78'. The distal long part 72' generally parallels to the longitudinal axis 58" of a second expansion strut 42" of a first expansion strut 42" pair in a second expansion column 42". However, the distal long part 72' can be made not to parallel to the longitudinal axis 58" of a second expansion strut 42" of a first expansion strut 42" pair in a second expansion column 32". A first connecting strut proximal section including the proximal stem 66', a junction 80', the long portion 68' and a first connecting strut distal section including the distal stem 70', a junction 82', the long portion 72' are mirror images to each other, as they are on the opposite ends of a diagonally aligned intermediate section 74' of a first connecting strut 44'. The proximal end 62' of the proximal short stem 66' and distal end 64' of the distal short stem 70' of a first connecting strut 44' points to opposite or different directions. The intermediate section 74' of a first connecting strut 44' traverses diagonally through the inter-connecting space separating the first closed expansion strut loop 48' in a first expansion strut column 32' and the first closed expansion strut loop 48" in a second expansion strut column 32". A proximal end 62' of a proximal short stem 68' of a first connecting strut 44' in a connecting strut column 34' is attached to an outer edge on the side of a stepped-down parallel notch 50' of a first expansion strut pair closed loop 48' and a distal end 64' of a distal short stem 70' of the first connecting strut 44' in a first connecting strut column 34' is contralaterally (compared to the proximal end 62' position) attached to an outer edge on the side of a stepped-up parallel notch 52" of a first expansion strut pair loop 48" in a second expansion column 32". In other words, a diagonally configured first connecting strut 44' has a proximal end 62' to the contralaterally located attachment sites 50' on the side of a distal stepped-down parallel notch of a first expansion strut 42' in a first expansion column 32' and a distal end 64' to the contralaterally located attachment site 52" on the side of a proximal stepped-up, parallel notch of a first expansion strut 42" in a second expansion column 32". An intermediate section 74' of a first connecting strut 44' in a first connecting strut column 34' is configured in a diagonally directed shape so that the proximal end 62' of the proximal stem 66' and the distal end 64' of the distal stem 70' of the connecting strut 44' would point to opposite directions to make optimum connections to the contralaterally located two coupling sites 50' and 52". The short proximal stem 66' is coupled at a perpendicular or slant angle to the proximal portion 68' of a first connecting strut 44' and to the distally located stepped-down parallel notch 50' of a first expansion strut 42' in a first expansion column 32'. Likewise, the short distal stem 70' is coupled at a perpendicular or slant angle to the distal portion 72' of a first connecting strut 44' and to the proximally located stepped-down parallel notch 50" of a first expansion strut 42" in a second expansion column 32'

This perpendicular or slant angle configuration of the proximal stem 66' or distal stem 70' of the first connecting strut 44' coupling to their respective contralaterally located attachment site 50' and attachment site 52" is designed to maximally enhance the longitudinal flexibility of the first connecting strut 44' between the first expansion column 32' and the second expansion column 32". The diagonally shaped connecting strut 44' is also designed to minimize the foreshortening of stent 10 when the stent 0 is expanded.

A third expansion column 32''' of stent 10 is made of a plurality of two adjacent companion expansion struts 42''' of horizontal alignment and a joining strut 46''' to form a closed loop slot 48''' at a proximal or distal end of an expansion strut 42''' pair. A joining strut 46''' forms a first corner 54''' where the joining strut 46''' joins a first expansion strut 42''' and a second corner 56''' is formed where the joining strut 46''' joins a second expansion strut 42''' of a third expansion strut 42''' pair. A proximal cell slot 38''' or a distal cell slot 40''' is formed inside a closed loop 48' of an expansion strut 42''' pair in a third expansion column 32'''. An expansion strut 42''' in a third expansion column 32''' is aligned horizontally, generally paralleling to the longitudinal axis 17 of the stent 10. Also first and second adjacent expansion struts 42''' in a third expansion column 32''' are aligned horizontally so that first and second expansion strut 42''' would parallel to each other. However, one of the two expansion strut 42''' in an expansion strut 42''' pair in a third expansion column 32''' may not parallel to the longitudinal axis 17 of the stent 10 or to the adjacent companion expansion strut 42'''. An expansion strut 42''' pair in a third expansion column 32''' has a stepped-down parallel notch 50''' outside on a distal or proximal end of an expansion strut 42''' pair near the closed loop 48''' and apart from a joining strut 46'''. A proximal or distal parallel stepped-down parallel notch 50''' is created to contralaterally attach a proximal 62 or distal end 64 of a diagonal connector 44 that connects to a third expansion column 32'''. A longitudinal axis 60''' of a parallel stepped-down notch 50''' parallels to a longitudinal axis 58''' of an expansion strut 42'''. In FIGS. 3 and 4, a third expansion column 32''' has twelve (12) closed loop 48''' expansion strut pairs in an unbroken fashion around the circumference 18 of the stent 10. Out of twelve (12) expansion strut pairs, six (6) of them have their closed loop 48''' pointed proximally and the other six (6) have their closed loops 48''' pointed distally in an alternating sequence. Therefor, each expansion strut 42' is connected to a closed loop 48''' on both ends. One closed loop 48''' on one end of an expansion strut 42''' points distally and other closed loop 48''' on the other end points proximally. The twelve (12) expansion strut closed loops 48''' in a third expansion column 32''', therefor, make a set of six (6) expansion strut pair cycles; with each expansion strut pair cycle consists of one closed loop 48''' on the proximal and one closed loop 48''' on the distal end. All the corners or angled areas in a third expansion column 32''' has their respective radius of curvature to minimize sharp corners as follows: a radius of curvature at a first corner 54''', a radius of curvature at a second corner 56''', a radius of curvature at a inner side of first corner 54''', a radius of curvature at a inner side of second corner 56''', a radius of curvature 92''' at an outer edge of a stepped-down parallel notch 50''' and a radius of curvature 84''' at an inner edge of a stepped-down parallel notch 50'''.

A second connecting column 34" is formed of a plurality of second connecting strut 44". A connecting strut 44" in a second connecting strut column 34" is a mirror image of a connecting strut 44' in a first connecting strut column 34'. Each connecting strut 44" in a second connecting strut column 34" includes a connecting strut proximal section, a connecting strut distal section and a connecting strut intermediate section 74'. A first connecting strut proximal section has two parts: a short stem 66" and a long portion 68". A proximal end 62" of proximal stem 66" is coupled at a perpendicular or slant angle to the contralateral out side of the distal stepped-up parallel notch 52" of a distal end of a second expansion strut 42" of a first expansion strut pair closed loop 48" of a second expansion column 32". A first connecting strut 44" proximal section portion 68" is coupled to the proximal stem 66" proximally in a junction 80" at a generally perpendicular or a slant angle, and a first connecting strut 44" proximal portion 68" is coupled to the intermediate section 74" distally in a junction 76" at a generally perpendicular or a slant angle. The proximal portion 68" generally parallels to the longitudinal axis 58" of a second expansion strut 42" of a second expansion column 32". However, the proximal portion 68" of a first connecting strut 44" can be made not to parallel to the longitudinal axis 58" of a second expansion strut 42" of a second expansion column 32". A first connecting strut 44" distal section also has two parts: a short distal stem 70" and a long portion 72". A first connecting strut 44" distal end 64" of distal stem 70" is coupled at a perpendicular or slant angle to the contralateral out side of the proximal stepped-down parallel notch 50''' in a proximal end of a first expansion strut 42''' of a third expansion column 32'''. A distal long portion 72" is coupled to the distal stem 70" distally in a junction 82" at a generally perpendicular or a slant angle, and is coupled to the intermediate section 74" proximally in a junction 78" at a generally perpendicular or a slant angle. The distal long portion 72" generally parallels to the longitudinal axis 58'" of a first expansion strut 42'" of a third expansion column 32'". However, the distal long portion 72" of a first connecting strut 44" in a second connecting strut column 34" can be made not to parallel to the longitudinal axis 58'" of a first expansion strut 42'" of a first expansion strut pair in a third expansion column 32'". A first connecting strut proximal section 66", 80", 68" and a first connecting strut distal section 70", 82", 72" are mirror images to each other on the opposite ends of a diagonally aligned intermediate section 74". The proximal end 62" and distal end 64" of a first connecting strut 44" points to opposite or different directions. A first connecting strut 44" intermediate section 74" proximal end is coupled at a slant angle in a junction 76" to the distal end of first connecting strut 44" proximal long portion 68" and a first connecting strut 44" intermediate section 74" distal end is coupled at a slant angle in a junction 78" to the proximal end of a first connecting strut 44" distal long portion 72". The intermediate section 74" of a first connecting strut 44" diagonally traverses through the interconnecting space separating the first closed loop 46" in a second expansion strut column 32" and the first closed loop 46'" in a third expansion strut column 32'". A proximal end 62" of a connecting strut 44" in a second connecting strut column 34" is attached to a step-up parallel notch 52" on the distal contralateral side of a second expansion strut 42" in a second expansion strut column 32" and a distal end 64" of a second connecting strut 44" is attached to a step-down parallel notch 50'" on the proximal contralateral side of a first expansion strut 42'" in a third expansion column 32'". In other words, a diagonally arranged positions of a proximal end 62" and a distal end 64" of a first connecting strut 44" in a second connecting strut column 34" connects the two contralerally located attachment sites on the outer-edge of a respective expansion strut 42" of a second expansion columns 32" and of a respective expansion strut 42'" of a third expansion column 32'". A connecting strut 44" in a second connecting strut column 34" is configured in a diagonal shape so that each end 62" and 64" would connect the two apposed and contralaterally located attachment sites 50'" and 52'" in a two adjacent expansion columns 32" and 32'" respectively. Particularly, the short proximal stems 66" and 70" of a connecting strut 44" in a second connecting strut column 34" has a perpendicular or slant angle to the long proximal part 68" and the long distal portion 72", and to the sides of the attached sites in the respective expansion struts 42" and 42'".

FIG. 3 is used to illustrate the serial connecting pattern of a first expansion column 32' to a second expansion column 32" by a first connecting strut column 34'; of a second expansion column 32" to a third expansion column 32'" by a second connecting strut column 34", and so forth in a repeated sequence to make a prescribed length of a tubular stent 10 of present invention by adding expansion columns 32 using connecting strut columns 34.

In a first expansion column 32' a first and second expansion struts 42' in a first expansion strut 42' pair are joined by a first joining strut 46' to form a closed strut pair loop 48' at a distal end of a first expansion strut 42' pair. A second expansion strut pair includes a third expansion strut 42' adjacent to a second expansion strut 42' and a second joining strut 48' to form a second closed loop 48' at a proximal end of a second expansion strut pair. A third expansion strut pair includes a fourth expansion strut 42' adjacent to a third expansion strut 42' and a third joining strut 46' to form a third closed loop 48' at a distal end of a third expansion strut 42' pair. A fourth expansion strut pair includes a fifth expansion strut 42' adjacent to a fourth expansion strut 42' and a fourth joining strut 46' to form a fourth closed loop 48' at a proximal end of a fourth expansion strut 42' pair. This first expansion column 32' building process is continued in a patterned sequence to complete a desired number expansion strut 42' pairs and closed loops 48' in a first expansion column 32'. In this figure a first expansion column 32' includes a twelve (12) expansion strut 42' pairs and a twelve (12) closed loops 48' in a patterned sequence. However, a number of closed loops 48' and expansion strut 42' pairs can be changed to more or less number according to the prescribed requirements of a tubular stent made for clinical use. This variation of setting a varying number of closed loops 48' and expansion strut 42' pairs in a stent 10 is within the scope of a tubular stent of present invention.

Each of the closed loop 48' expansion strut 42' pair in a first expansion column 32' has a stepped-down parallel notch 50' for a contralateral attachment of an end of a diagonal connector strut 44', either at a distal or a proximal end of an expansion strut 42' pair. A first stepped-down parallel notch 50' in a first expansion column 32' is formed at a distal end of a first closed loop 48' expansion strut pair. A second stepped-down parallel notch 50' in a first expansion column 32' is formed at a proximal end of a second closed loop 48' expansion strut pair. A third step-down parallel notch 50' in a first expansion column 32' is formed at a distal end of a third closed loop 48' expansion strut pair. A fourth stepped-down parallel notch 50' in a first expansion column 32' is formed at a proximal end of a fourth closed loop 48' expansion strut 42' pair. This stepped-down parallel notch 50' building process is continued in a patterned sequence to complete a desired number of step-down parallel notches 50' in a first expansion column 32'. In this figure, a first expansion column 32' includes a twelve (12) stepped-down parallel notches 50'. A stepped-down parallel notch 50' in a first expansion strut 42' is a short horizontal segment with an outer side adjacent to a first closed loop 48'. The longitudinal axis 60' of a stepped-down parallel notch 50' is parallel to the longitudinal axis 58' of the proximal portion of the first expansion strut 42' in a first expansion column 32'. All the stepped-down parallel notches 50' in a first expansion column 32' generally parallels to the longitudinal axes 58' of the respective expansion struts 42'; although a stepped-down parallel notch 50' does not have to parallel to the longitudinal axis 58' of a respective expansion struts 42'. The variation of parallel versus non-parallel axis of a stepped-down parallel notch 50' with the axis 58' in a first expansion strut 42' is within the scope of a tubular stent 10 of present invention.

In a second expansion column 32" a first and second expansion struts 42" in a first expansion strut pair are joined by a first joining strut 46" to form a closed strut loop 48" at a proximal end of a first expansion strut 42" pair. A second expansion strut pair includes a third expansion strut 42" adjacent to a second expansion strut 42" and a second joining strut 46" to form a second closed strut loop 48' at a distal end of a second expansion strut pair. A third expansion strut pair includes a fourth expansion strut 42" adjacent to a third expansion strut 42" and a third joining strut 46" to form a third closed strut loop 48" at a proximal end of a third expansion strut 42" pair. A fourth expansion strut pair includes a fifth expansion strut 42" adjacent to a fourth expansion strut 42" and a fourth joining strut 46" to form a fourth closed strut loop 48" at a distal end of a fourth expansion strut 42" pair. This second expansion column 32" building process is continued in a patterned sequence to complete a desired number expansion strut 42" pairs and closed strut loops 48" in a second expansion column 32". In this figure a first expansion column 32" includes a twelve

(12) expansion strut 42" pairs and a twelve (12) closed strut loops 48" in a patterned sequence. However, a number of closed loops 48" and expansion strut 42" pairs can be changed to more or less number according to the prescribed requirements of a tubular stent made for clinical use. This variation of setting a varying number of closed loops 48" and expansion strut 42" pairs in a stent 10 is within the scope of a tubular stent of present invention.

Each of the closed loop 48" and expansion strut 42" pair in a second expansion column 32" has a stepped-up parallel notch 52" for a contralateral attachment of an end of a diagonal connector strut 44", either at a distal or a proximal end of an expansion strut 42" pair. A first stepped-up parallel notch 52" in a second expansion column 32" is formed at a distal end of a first expansion strut closed loop 48". A second stepped-up parallel notch 52" in a first expansion column 32' is formed at a proximal end of a second closed loop 48" expansion strut pair. A third step-up parallel notch 52" in a first expansion column 32' is formed at a distal end of a third closed loop 48" expansion strut pair. A fourth stepped-up parallel notch 52" in a first expansion column 32' is formed at a proximal end of a fourth closed loop 48" expansion strut 42" pair. This stepped-up parallel notch 52" building process is continued in a patterned sequence to complete a desired number of step-up parallel notches 52" in a first expansion column 32'. In this figure, a second expansion column 32" includes a twelve (12) stepped-up parallel notches 52". A stepped-up parallel notch 52" in a second expansion strut 42" is a short horizontal segment with an outer side or edge, adjacent to a first closed loop 48". The longitudinal axis 60" of a stepped-up parallel notch 52" is parallel to the longitudinal axis 58', of the proximal portion of same expansion strut 42" in a first expansion column 32'. All the stepped-up parallel notches 52" in a second expansion column 32" generally parallels to the longitudinal axes 58" of the respective expansion struts 42"; although a stepped-up parallel notch 52" does not have to parallel to the longitudinal axes 58" of a respective expansion struts 42". The variation of parallel versus non-parallel axis of a stepped-up parallel notch 52' with the axis 58' in a second expansion strut 42" is within the scope of a tubular stent 10 of present invention.

In a third expansion column 32''' a first and second expansion struts 42''' in a first expansion strut 42''' pair are joined by a first joining strut 46' to form a closed strut pair loop 48''' at a proximal end of a first expansion strut 42''' pair. A second expansion strut pair includes a third expansion strut 42''' adjacent to a second expansion strut 42''' and a second joining strut 46''' to form a second closed loop 48''' at a distal end of a second expansion strut pair. A third expansion strut pair includes a fourth expansion strut 42''' adjacent to a third expansion strut 42''' and a third joining strut 46''' to form a third closed loop 48''' at a proximal end of a third expansion strut 42''' pair. A fourth expansion strut pair includes a fifth expansion strut 42''' adjacent to a fourth expansion strut 42''' and a fourth joining strut 46''' to form a fourth closed loop 48' at a distal end of a fourth expansion strut 42''' pair. This third expansion column 32''' building process is continued in a patterned sequence to complete a desired number expansion strut 42''' pairs and closed loops 48''' in a third expansion column 32'''. In this figure a third expansion column 32''' includes a twelve (12) expansion strut 42''' pairs and a twelve (12) closed loops 48''' in a patterned sequence. However, a number of closed loops 48''' and expansion strut 42''' pairs can be changed to more or less number according to the prescribed requirements of a tubular stent made for clinical use. This variation of setting a varying number of closed loops 48''' and expansion strut 42''' pairs in a stent 10 is within the scope of a tubular stent of present invention.

Each of the closed loop 48''' expansion strut 42''' pair in a third expansion column 32''' has a stepped-down parallel notch 50''' for a contralateral attachment of an end of a diagonal connector strut 44, either at a distal or a proximal end of an expansion strut 42 pair. A first stepped-down parallel notch 50' in a third expansion column 32''' is formed at a proximal end of a first closed loop 48''' expansion strut pair. A second stepped-down parallel notch 50''' in a third expansion column 32''' is formed at a distal end of a second closed loop 48''' expansion strut pair. A third step-down parallel notch 50''' in a third expansion column 32''' is formed at a proximal end of a third closed loop 48''' expansion strut pair. A fourth stepped-down parallel notch 50''' in a third expansion column 32''' is formed at a distal end of a fourth closed loop 48''' expansion strut 42''' pair. This stepped-down parallel notch 50''' building process is continued in a patterned sequence to complete a desired number of step-down parallel notches 50''' in a third expansion column 32'''. In this figure, a third expansion column 32''' includes a twelve (12) stepped-down parallel notches 50'''. A stepped-down parallel notch 50''' in a first expansion strut 42''' pair is a short horizontal segment with an outer side adjacent to a first closed loop 48'''. The longitudinal axis 60' of a stepped-down parallel notch 50''' is parallel to the longitudinal axis 58''' of the distal long portion of the first expansion strut 42''' in a third expansion column 32'''. All the stepped-down parallel notches 50''' in a third expansion column 32''' generally parallels to the longitudinal axes 58''' of the respective expansion struts 42'''; although a stepped-down parallel notch 50''' does not have to parallel to the longitudinal axis 58''' of a respective expansion struts 42'''. The variation of parallel versus non-parallel axis of a stepped-down parallel notch 50''' with the axis 58' in a first expansion strut 42''' is within the scope of a tubular stent 10 of present invention.

There are six connecting struts 44' in a first connecting strut column 34', with the first connecting strut 44' at the top and the sixth connecting strut 44' at the bottom of the first connecting strut column 34' in FIG. 3. The first connecting column 34' connects the first expansion column 32' and the second expansion strut 42' column 32" in an unbroken fashion to form a tubular sub-unit with a longitudinal axis 17 of a tubular stent 10 of present invention. When a first connecting column 34' connects a first expansion column 32' to a second expansion column 32", six (6) closed stent cells 36' are formed. Each of these stent cells 36' is completely closed by a combination of expansion struts 42' and joining struts 46' in a first expansion column 32', the expansion struts 42" and joining struts 46" in a second expansion column 32" and two connecting strut 44' in a first connecting strut column 34'. A stent cell 36' in a stent 10 has one cell slot 38' in the proximal end and one cell slot 40" in the distal end. In a first expansion column 32', a proximal cell slot 38' is located in juxtaposition with an adjacent distal cell slot 40'. Likewise in a second expansion column 32", a distal cell slot 40" is located in juxtaposition with an adjacent proximal cell slot 38". A closed stent cell formed between the first 32' and second 32" expansion columns with a first connecting column 34' has an asymmetrical cell geometry in this unexpanded stent pattern.

In the second connecting column 34" also has six connecting struts 44" in a second connecting strut column 34", with the first connecting strut 44" at the top and the sixth connecting strut 44" at the bottom of a second connecting strut column 34" in FIG. 3. The second connecting column 34" couples the second expansion column 32" to the third expansion column 32'" in an unbroken fashion to form a tubular sub-unit with a longitudinal axis 17 in a tubular stent 10 of present invention. When a second connecting column 34" connects a second expansion column 32" to a third expansion column 32'", six (6) closed stent cells 36" are formed. Each of these stent cells 36" is completely closed by a combination of expansion struts 42" and joining struts 46" in a second expansion column 32", expansion struts 42'" and joining struts 46'" in a third expansion column 32'" and two connecting struts 44" in a second connecting strut column 34". A stent cell 36" in a stent 10 has one cell slot 38" in the proximal end and one cell slot 40'" in the distal end. In a second expansion column 32", a proximal cell slot 38" is located in juxtaposition with an adjacent distal cell slot 40". Likewise in a third expansion column 32'", a distal cell slot 40'" is located in juxtaposition with an adjacent proximal cell slot 38'". A closed stent cell formed between the second 32" and third 32'" expansion columns and a second connecting column 34" has an asymmetrical cell geometry in this unexpanded stent pattern.

Figure 4A:
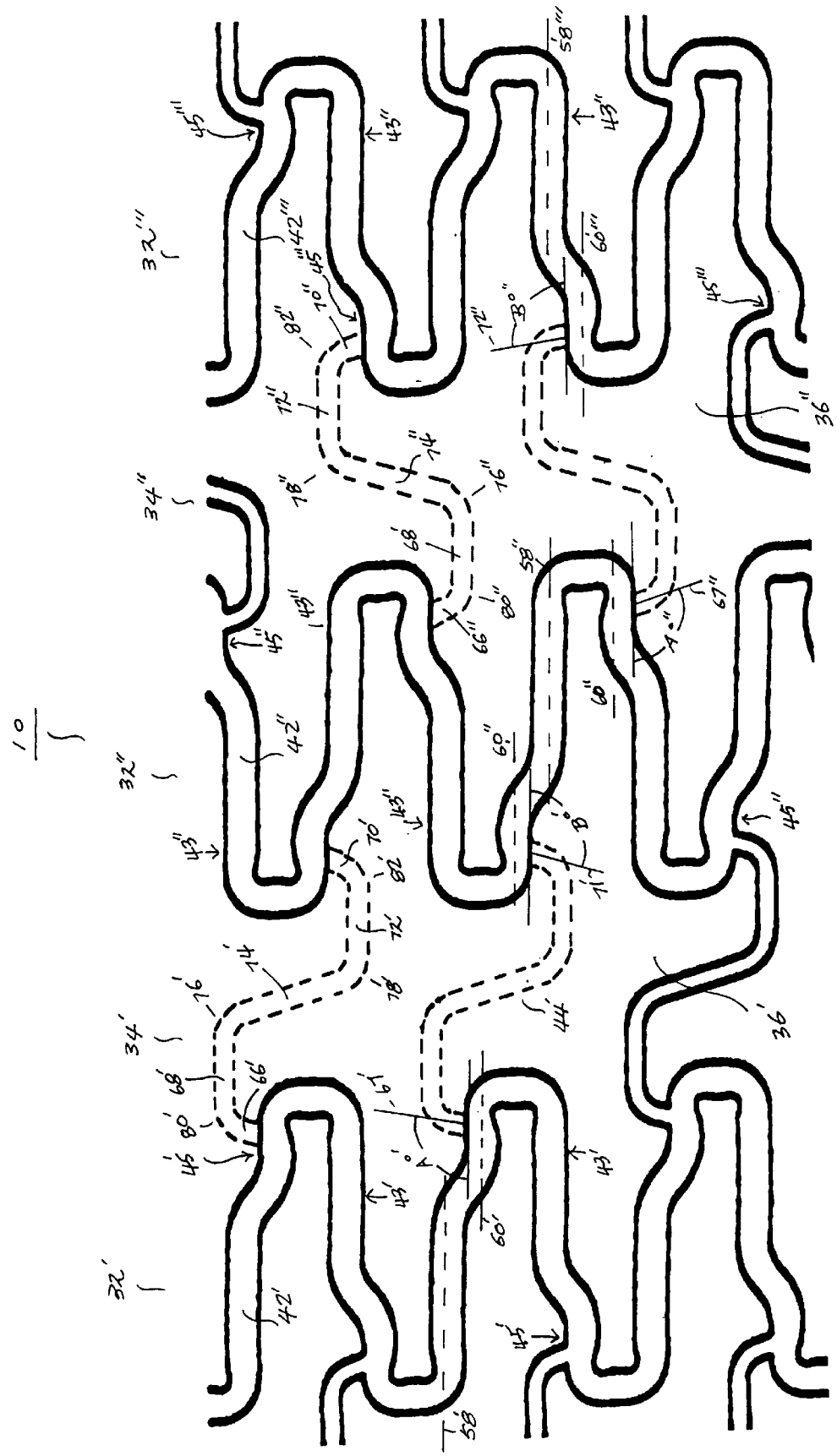
FIG. 4a—A magnified view of the unexpanded 2-dimensional cut-open stent 10 detailing how the proximal 66 and distal 70 stems of the connector strut 44 couples to the sides 45 of the expansion 42 struts.

FIG. 4a illustrates how the proximal and distal ends of a connecting strut 44 couples to the sides of the respective expansion struts 42'. In a first connecting column 34', a first connecting strut 44' is drawn in dotted line to better illustrate how proximal stem 66' and distal stem 70' are coupled to the sides of their respective struts 42', 42". The axis 67' of proximal stem 66' of a first connecting strut 44' and the axis 60' of the distal stepped-down parallel notch 50' form an angle A' nearest to the stepped transition. An angle A' is preferably 90 degrees or greater but can be less than 90 degrees. The axis of outer edge 45' of the stepped-down parallel notch 50' parallels to the axis 60' of the same segment 50'. The joining angle A' between the axis 67' and axis 60' is generally similar to the joining angle A' between the axis 67' and the plane of the outer edge 45' of the stepped parallel notch 50'. Similar relationship is repeated in the distal stem 70' of a first connecting strut 44'. The axis 71' of distal stem 70' of a first connecting strut 44' and the axis 60" of the a stepped-up parallel notch 52" form an angle B' nearest to the stepped transition. An angle B' is preferably 90 degrees or greater but can be less than 90 degrees. The axis of outer edge 45" of the stepped-up parallel notch 52" parallels to the axis 60" of the same segment 52". The joining angle B' between the axis 71' and axis 60" is generally similar to the joining angle B' between the axis 71' and the plane of the outer edge 45" of the stepped parallel notch 52". A proximal stem 67' clearly joins to the outer edge 45' on the side of a stepped parallel notch 50' with an axis 60' of a first expansion strut 42' in a first expansion column 32'. Likewise, the distal stem 70' clearly joins to the outer edge 45" of the stepped parallel notch 52" with an axis 60" of a first expansion strut 42" in a second expansion column 32".

In a second connecting column 34", a second connecting strut 44" is drawn in dotted line to better illustrate how proximal stem 66" and distal stem 70" are coupled to the sides of their respective struts 42", 42'". The axis 67" of proximal stem 66" of a second connecting strut 44" and the axis 60" of the distal stepped-up parallel notch 52" form an angle A" nearest to the stepped transition. An angle A" is preferably 90 degrees or greater but can be less than 90 degrees. The axis of outer edge 45" of the stepped-up parallel notch 52" parallels to the axis 60" of the same segment 52". The joining angle A" between the axis 67" and axis 60" is generally similar to the joining angle A" between the axis 67' and the plane of the outer edge 45' of the same stepped parallel notch 52". Similar relationship is repeated in the distal stem 70" of a second connecting strut 44". The axis 71" of distal stem 70" of a second connecting strut 44" and the axis 60" of the a stepped-up parallel notch 52" form an angle B" nearest to the stepped transition. An angle B" is preferably 90 degrees or greater but can be less than 90 degrees. The axis of outer edge 45" of the stepped-up parallel notch 52" parallels to the axis 60" of the same segment 52". The joining angle B" between the axis 71' and axis 60" is generally similar to the joining angle B" between the axis 71' and the plane of the outer edge 45" of the stepped parallel notch 52". A proximal stem 67" clearly joins to the outer edge 45" on the side of a stepped parallel notch 52" with an axis 60" of a first expansion strut 42" in a second expansion column 32". Likewise, the distal stem 70" clearly joins to the outer edge 45" of the stepped parallel notch 52'" with an axis 60'" of a first expansion strut 42'" in a third expansion column 32'".

Figure 4B:
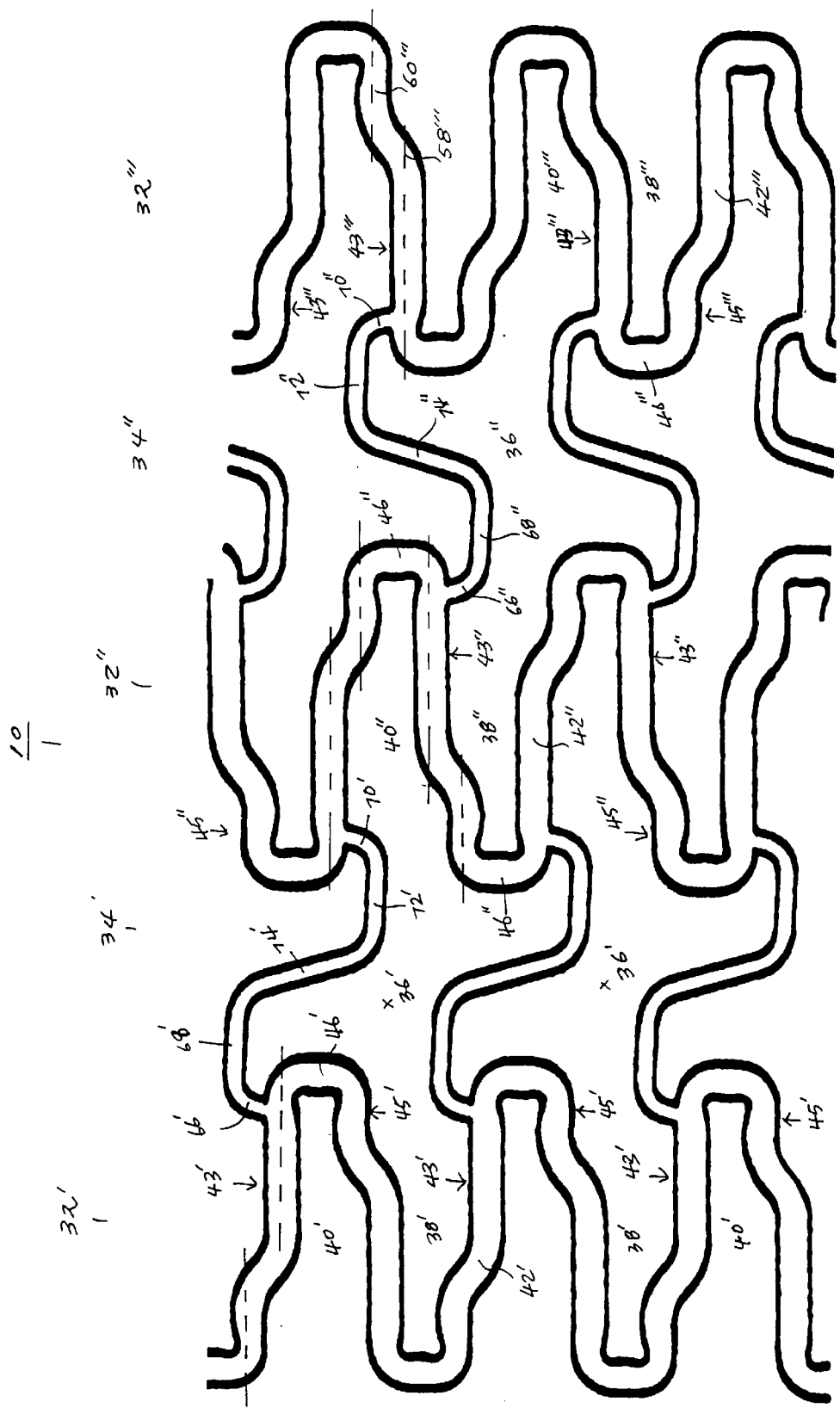

FIG. 4b illustrates an alternative coupling of the proximal stem 66 and distal stem 70 of a connecting strut 44 to the contralateral outer side of the opposing expansion strut closed loops 48 in two adjacent expansion columns 32. In a first connecting column 34', a proximal stem 66' of a first connecting strut 44' in a first connecting column 34' is attached to the outer side 43' of the distal long portion with longitudinal axis 58' of a first expansion strut 42' of a first expansion strut pair in a first expansion column 32'. This attachment configuration is drastically different from the examples discussed in FIGS. 4 and 4a. In this configuration of FIG. 4b, the proximal stem 66' is attached to a contralateral outside edge 43' on a distal end of a first expansion strut 42' opposite from a distal stepped-up parallel notch 52' of a first expansion strut pair closed loop 48'. Likewise, a distal stem 70' of a first connecting strut 44' in a first connecting column 34' is attached to the outer side 43" of the proximal long portion with longitudinal axis 58" of a second expansion strut 42" of a first expansion strut pair in a second expansion column 32". This attachment configuration of the distal stem 70' to the distal long portion of a first expansion strut 42" in a second expansion column 32" is different from the examples discussed in FIGS. 4 and 4a. In this configuration of FIG. 4b, the distal stem 70' is attached to a contralateral outside edge 43" on a distal end of a second expansion strut 42" opposite from a proximal stepped-down parallel notch 52" of a first expansion strut pair closed loop 48".

In a second connecting column 34", a proximal stem 66" of a first connecting strut 44" in a second connecting column 34" is attached to the outer side 43" of the distal long portion with longitudinal axis 58" of a second expansion strut 42" of a first expansion strut pair in a second expansion column 32". This attachment configuration is distinctly different from the examples discussed in FIGS. 4 and 4a. In this configuration of FIG. 4b, the proximal stem 66" is attached to a contralateral outside edge 43" on a distal end of a second expansion strut 42" opposite from a distal stepped-down parallel notch 50" of a first expansion strut pair closed loop 48". Likewise, a distal stem 70" of a second connecting strut 44" in a second connecting column 34" is attached to the outer side 43'" of the proximal long portion with longitudinal axis 58" of a first expansion strut 42'" of a first expansion strut pair in a third expansion column 32'". This attachment configuration of the distal stem 70" to the distal long portion of a first expansion strut 42'" in a third expansion column 32'" is different from the examples discussed in FIGS. 4 and 4a. In this configuration of FIG. 4b, the distal stem 70' is attached to a contralateral outside edge 43'" on a proximal end of a first expansion strut 42''' opposite from a proximal stepped-down parallel notch 52" of a first expansion strut pair closed loop 48". These alternative connector attachment configurations are within the scope of stent 10 of present invention.

The configuration specifics of expansion strut 42 pairs and closed expansion loops 48 in a first 32', second 32" and third 32''' expansion columns of the alternative design depicted in FIG. 4b are exactly same as the specifications detailed in FIGS. 3, 4 and 4a. The shape and attachment details of first 44' and second 44" connecting struts in a first 34' and second 34" connecting columns are also exactly same as detailed in FIGS. 3 and 4.

Figure 5:
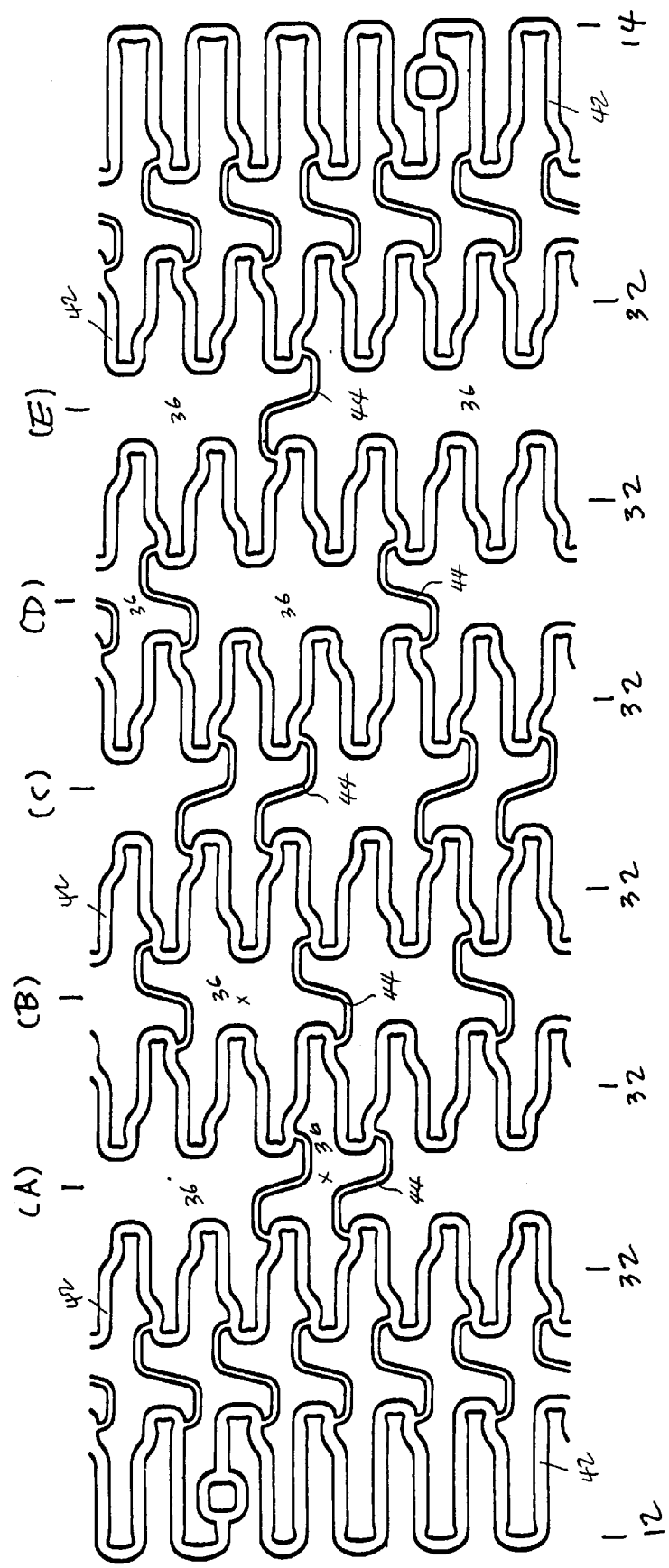
FIG. 5—A cut-open 2-dimensional view of stent 10 of present invention illustrating the skipped connector attachments of at least 5 variations.

FIG. 5 illustrates examples of how skipped connector links between two adjacent expansion columns (32) can be created. Skipped connector pattern can be utilized when more flexibility is desired in a stent 10 made for clinical use. The more connectors are removed, the more flexible the stent 10 becomes. However, as the number of skipped connector (44) increase, the vessel-cover of a stent 10 suffers proportionally. As the number of skipped connector link increase, the axio-lateral strength of the stent also suffers increasingly.

In a connector column (A) in FIG. 5, there are only two (2) consecutive connectors 44 linking the two adjacent expansion columns 32. In a connector column (B), there are three (3) connectors 44 linking the two adjacent expansion columns 32, interposed by a skipped connector between the three connectors 44. In a connector column (C), there is a pair of two consecutive connectors 44 separated by single unconnected link between the pair of two consecutive connectors 44. In a connector column (D), there are two (2) connectors linking the two adjacent expansion columns 32, separated by two skipped connectors between them. In a connector column (E), there is only one connector 44 linking the two adjacent expansion columns 32.

In a skipped connector design, stent 10 can have only one of these five (5) skipped link pattern through out the stent 10, or combination of more than one skipped pattern in a stent 10. All five of these skipped connector 44 liking pattern are within the scope of stent 10 of present invention.

The foregoing description of a preferred embodiment of the invention has been presented for purposes of illustration and description. It is not intended to be exhaustive or to limit the invention to the precise forms disclosed. Obviously, many modifications and variations will be apparent to practitioners skilled in this art. It is intended that the scope of the invention be defined by the following claims and their equivalents.

I claim:

1. A circumferentially connected stent in a non-expanded state with a longitudinal axis, comprising:
   a plurality of expansion struts forming a first expansion column, the first expansion column including a first expansion strut, a second expansion strut and a first joining strut coupling a distal end of the first expansion strut to a distal end of the second expansion strut, the first expansion strut having a stepped distal portion and the second expansion strut having a stepped proximal portion;
   a plurality of expansion struts defining a second expansion column, the second expansion column including a first expansion strut, a second expansion strut and a first joining strut coupling a distal end of the first expansion strut to a distal end of the second expansion strut, the first expansion strut having a stepped proximal portion and the second expansion strut having a stepped distal portion; and
   a first serial connecting strut column formed of a plurality of serial connecting struts and including a first serial connecting strut, the first serial connecting strut column coupling the first expansion column to the second expansion column.

2. The stent of claim 1, wherein the first and second expansion columns and the first serial connecting strut column form asymmetric cells.

3. The stent of claim 2, wherein each of an asymmetric cell includes a proximal slot formed between a pair of adjacent expansion struts in the first expansion column and a distal slot formed between a pair of adjacent expansion struts in the second expansion column.

4. The stent of claim 1, wherein each of the serial connecting struts in the first serial connecting strut column has a proximal portion coupled to a proximal stem, a distal portion coupled to a distal stem and an intermediate portion that couples the proximal and distal portions of the serial connecting strut.

5. The stent of claim 4, wherein each intermediate portion of a serial connecting strut in the first serial connecting strut column diagonally couples the proximal and distal portions of the serial connecting strut.

6. The stent of claim 1, wherein the first serial connecting strut contralaterally couples the stepped distal portion of the first expansion strut of the first expansion column to the stepped proximal portion of the first expansion strut of the second expansion column.

7. The stent of claim 4, wherein the proximal stem of the first serial connecting strut is contralaterally coupled to the stepped distal portion of the first expansion strut of the first expansion column, and the distal stem of the first serial connecting strut is contralaterally coupled to the stepped proximal portion of the first expansion strut of the second expansion column.

8. The stent of claim 4, wherein the proximal stem of the first serial connecting strut is contralaterally coupled to a side of the stepped distal portion of the first expansion strut of the first expansion column, and the distal stem of the first serial connecting strut is contralaterally coupled to a side of the stepped proximal portion of the first expansion strut of the second expansion column.

9. The stent of claim 8, wherein in the first expansion column, the proximal portion of the first expansion strut has a longitudinal axis that is parallel to a longitudinal axis of the stepped distal portion of the first expansion strut.

10. The stent of claim 9, wherein in the second expansion column, the stepped proximal portion of the first expansion strut has a longitudinal axis that is parallel to a longitudinal axis of the distal portion of the first expansion strut.

11. The stent of claim 9, wherein the longitudinal axis of the proximal portion of the first expansion strut in the first expansion column is parallel to the longitudinal axis of the distal portion of the second expansion strut in the first expansion column.

12. The stent of claim 9, wherein in the first expansion column, a first side of the proximal portion of the first expansion strut has a same longitudinal axis as a first side of the proximal portion of the first serial connecting strut in the first serial strut connecting column.

13. The stent of claim 12, wherein in the first expansion column a second side of the distal portion of the second expansion strut has a same longitudinal axis as a second side of a distal portion of the first serial connecting strut in the first serial strut connecting column.

14. The stent of claim 13, wherein in the second expansion column a second side of the distal portion of the first expansion strut has a same longitudinal axis as the second side of the distal portion of the first serial connecting strut in the first serial strut connecting column.

15. A circumferentially connected stent in a non-expanded state with a longitudinal axis, comprising:
   a plurality of expansion struts forming a first expansion column, the first expansion column including a first expansion strut, a second expansion strut and a first joining strut coupling a distal end of the first expansion strut to a distal end of the second expansion strut, the first expansion strut having a stepped distal portion and the second expansion strut having a stepped proximal portion;
   a plurality of expansion struts defining a second expansion column, the second expansion column including a first expansion strut, a second expansion strut and a first joining strut coupling a distal end of the first expansion strut to a distal end of the second expansion strut, the first expansion strut having a stepped proximal portion and the second expansion strut having a stepped distal portion;
   a first serial connecting strut column formed of a plurality of serial connecting struts and including a first serial connecting strut, the first serial connecting strut column coupling the first expansion column to the second expansion column;
   a plurality of expansion struts forming a third expansion column, the third expansion column including a first expansion strut, a second expansion strut and a first joining strut coupling a proximal end of the first expansion strut to a proximal end of the second expansion strut, the first expansion strut having a stepped proximal portion and the second expansion strut having a stepped distal portion; and
   a second serial connecting strut column formed of a plurality of connecting struts including a first serial connecting strut, the first serial connecting strut column coupling the second expansion column to the third expansion column.

16. The stent of claim 15, wherein the first and second expansion columns and the first serial connecting strut column form a first set of asymmetric cells, and the second and third expansion columns and the second serial connecting strut column form a second set of asymmetric cells.

17. The stent of claim 16, wherein each of a first set of an asymmetric cell includes a proximal cell slot formed between a pair of adjacent expansion struts in the first expansion column and a distal cell slot formed between a pair of adjacent expansion struts in the second expansion column.

18. The stent of claim 17, wherein each of a second set of an asymmetric cell includes a proximal cell cell slot formed between a pair of adjacent expansion struts in the second expansion column and a distal slot formed between a pair of adjacent expansion struts in the second expansion column.

19. The stent of claim 15, wherein each of the serial connecting struts in the first and second serial connecting strut columns has a proximal portion with a proximal stem, a distal portion with a distal stem and an intermediate portion that couples the proximal and distal portions.

20. The stent of claim 15, wherein the intermediate portion of each of the serial connecting struts of the first serial connecting strut column diagonally couples the proximal and distal portions.

21. The stent of claim 20, wherein the intermediate sections of the serial connecting struts of the first serial connecting strut column all extend in the same direction.

22. The stent of claim 21, wherein the intermediate sections of the serial connecting struts of the second serial connecting strut column all extend in the same direction.

23. The stent of claim 22, wherein the intermediate sections of the serial connecting struts of the first and second serial connecting strut columns extend in different directions.

24. The stent of claim 23, wherein only a portion of the expansion struts in the first expansion strut column are coupled by serial connecting struts in the first serial connecting strut column to expansion struts in the second expansion strut column.

25. The stent of claim 24, wherein only a portion of the expansion struts in the second expansion strut column are coupled by serial connecting struts in the second serial connecting strut column to expansion struts in the third expansion strut column.

26. The stent of claim 20, wherein the first serial connecting strut of the first serial connecting strut column contralaterally couples the stepped distal portion of the first expansion strut of the first expansion column to the stepped proximal portion of the first expansion strut of the second expansion column.

27. The stent of claim 26, wherein the proximal stem of the first serial connecting strut in the first serial connecting strut column is coupled to a side of the stepped distal portion of the first expansion strut in the first expansion column, and the distal stem of the first serial connecting strut is coupled to a side of the stepped proximal portion of the first expansion strut in the second expansion column.

28. The stent of claim 27, wherein the proximal stem of the first serial connecting strut in the first serial connecting strut column is coupled to the side of the stepped distal portion of the first expansion strut in the first expansion column at a connect angle of 85° or greater, wherein the connect angle is formed closest to a step formed in the first expansion strut of the first expansion column.

29. The stent of claim 28, wherein the proximal stem of the first serial connecting strut in the first serial connecting strut column is coupled to the side of the stepped distal portion of the first expansion strut in the first expansion column at a connect angle of 90° or greater, wherein the connect angle is formed closest to a step formed in the first expansion strut of the first expansion column.

30. The stent of claim 29, wherein the distal stem of the first serial connecting strut in the first serial connecting strut column is coupled to the side of the stepped proximal portion of the first expansion strut in the second expansion column at a connect angle of 85° or greater, wherein the connect angle is formed closest to a step formed in the first expansion strut of the second expansion column.

31. The stent of claim 29, wherein the distal stem of the first serial connecting strut in the first serial connecting strut column is coupled to the side of the stepped proximal portion of the first expansion strut in the second expansion column at a connect angle of 90° or greater, wherein the connect angle is formed closest to a step formed in the first expansion strut of the second expansion column.

32. The stent of claim 27, wherein the first serial connecting strut of the second serial connecting strut column contralaterally couples the stepped distal portion of the second expansion strut of the second expansion column to the stepped proximal portion of the first expansion strut of the third expansion column.

33. The stent of claim 32, wherein the proximal stem of the first serial connecting strut in the second serial connecting strut column is coupled to a side of the stepped distal portion of the second expansion strut in the second expansion column, and the distal stem of the first serial connecting strut in the second serial connecting strut column is coupled to a side of the stepped proximal portion of the first expansion strut in the third expansion column.

34. The stent of claim 33, wherein the proximal stem of the first serial connecting strut in the second serial connecting strut column is coupled to the side of the stepped distal portion of the second expansion strut in the second expansion column at a connect angle of 85° or greater, wherein the connect angle is formed closest to a step formed in the second expansion strut of the second expansion column.

35. The stent of claim 33, wherein the proximal stem of the first serial connecting strut in the second serial connecting strut column is coupled to the side of the stepped distal portion of the second expansion strut in the second expansion column at a connect angle of 90° or greater, wherein the connect angle is formed closest to a step formed in the second expansion strut of the second expansion column.

36. The stent of claim 33, wherein the distal stem of the first serial connecting strut in the second serial connecting strut column is coupled to the side of the stepped proximal portion of the first expansion strut in the third expansion column at a connect angle of 85° or greater, wherein the connect angle is formed closest to a step formed in the first expansion strut of the third expansion column.

37. The stent of claim 33, wherein the distal stem of the first serial connecting strut in the second serial connecting strut column is coupled to the side of the stepped proximal portion of the first expansion strut in the third expansion column at a connect angle of 90° or greater, wherein the connect angle is formed closest to a step formed in the first expansion strut of the third expansion column.

38. The stent of claim 19, wherein the first and second expansion columns and the first connecting strut column form a first set of asymmetric cells, and the second and third expansion columns and the second connecting strut column form a second set of asymmetric cells.

39. A circumferentially connected stent in a non-expanded state with a longitudinal axis, comprising:
    a plurality of expansion struts forming a first expansion column, the first expansion column including a first expansion strut, a second expansion strut and a first joining strut coupling a distal end of the first expansion strut to a distal end of the second expansion strut, the first expansion strut having a stepped proximal portion and the second expansion strut having a stepped distal portion;
    a plurality of expansion struts defining a second expansion column, the second expansion column including a first expansion strut, a second expansion strut and a first joining strut coupling a distal end of the first expansion strut to a distal end of the second expansion strut, the first expansion strut having a stepped distal portion and the second expansion strut having a stepped proximal portion; and
    a first serial connecting strut column formed of a plurality of serial connecting struts and including a first serial connecting strut, the first serial connecting strut column coupling the first expansion column to the second expansion column.

40. The stent of claim 39, wherein the first and second expansion columns and the first serial connecting strut column form asymmetric cells.

41. The stent of claim 40, wherein each of an asymmetric cell includes a proximal slot formed between a pair of adjacent expansion struts in the first expansion column and a distal slot formed between a pair of adjacent expansion struts in the second expansion column.

42. The stent of claim 39, wherein each of the serial connecting struts in the first serial connecting strut column has a proximal portion with a proximal stem, a distal portion with a distal stem and an intermediate portion that couples the proximal and distal portions of the serial connecting strut.

43. The stent of claim 42, wherein each intermediate portion of a serial connecting strut in the first serial connecting strut column diagonally couples the proximal and distal portions of the serial connecting strut.

44. The stent of claim 43, wherein the first serial connecting strut contralaterally couples the distal portion of the first expansion strut of the first expansion column to the proximal portion of the first expansion strut of the second expansion column.

45. The stent of claim 41, wherein the proximal stem of the first serial connecting strut is contralaterally coupled to the distal portion of the first expansion strut of the first expansion column, and the distal stem of the first serial connecting strut is contralaterally coupled to the proximal portion of the first expansion strut of the second expansion column.

46. The stent of claim 42, wherein the proximal stem of the first serial connecting strut is contralaterally coupled to a side of the distal portion of the first expansion strut of the first expansion column, and the distal stem of the first serial connecting strut is contralaterally coupled to a side of the proximal portion of the first expansion strut of the second expansion column.

47. The stent of claim 46, wherein in the first expansion column, the distal portion of the first expansion strut has a longitudinal axis that is parallel to a longitudinal axis of the proximal portion of the second expansion strut.

48. The stent of claim 47, wherein in the second expansion column, the proximal portion of the first expansion strut has a longitudinal axis that is parallel to a longitudinal axis of the distal portion of the second expansion strut.

49. The stent of claim 48, wherein the distal portion of the first expansion strut in the first expansion column has a longitudinal axis that is parallel to a longitudinal axis of the proximal portion of the first expansion strut in the second expansion column.

* * * * *